United States Patent [19]

Paget et al.

[11] Patent Number: 5,649,979
[45] Date of Patent: Jul. 22, 1997

[54] PROCESS FOR PERFUMING TEXTILES

[75] Inventors: Walter Paget, Versoix; Daniel Reichlin, Confignon, both of Switzerland; Roger Leslie Snowden, Viry, France; Eric C. Walborsky, Bridgewater, N.J.; Christian Vial, Geneva, Switzerland

[73] Assignee: Firmenich S.A., Geneva, Switzerland

[21] Appl. No.: 403,808

[22] PCT Filed: Jul. 28, 1994

[86] PCT No.: PCT/IB94/00228

§ 371 Date: Mar. 16, 1995

§ 102(e) Date: Mar. 16, 1995

[87] PCT Pub. No.: WO95/04809

PCT Pub. Date: Feb. 16, 1995

[30] Foreign Application Priority Data

Aug. 9, 1993 [CH] Switzerland ............... 2363/93

[51] Int. Cl.$^6$ ............... D06M 13/00; C11D 3/50
[52] U.S. Cl. ............... 8/137; 252/8.63; 510/320; 510/515; 510/101; 510/102
[58] Field of Search ............... 8/137; 252/8.6, 252/174.11

[56] References Cited

U.S. PATENT DOCUMENTS

| | | | |
|---|---|---|---|
| 4,201,680 | 5/1980 | Waltenberger et al. | 252/8.6 |
| 4,297,407 | 10/1981 | Manca | 252/8.6 |
| 5,445,747 | 8/1995 | Kvietok et al. | 252/8.6 |

FOREIGN PATENT DOCUMENTS

| | | |
|---|---|---|
| 397 345 A2 | 11/1990 | European Pat. Off. |
| 430 315 A2 | 6/1991 | European Pat. Off. |

Primary Examiner—Jacqueline V. Howard
Attorney, Agent, or Firm—Pennie & Edmonds

[57] ABSTRACT

We describe a process for perfuming fabrics washed in the presence of a lipase-containing detergent and, optionally, subsequently treated with a fabric softener, said process being characterized in that said detergent and/or said fabric softener contains a compound of formula

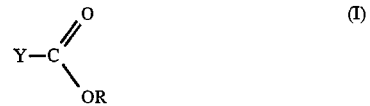

wherein a. R represents a radical derived from an fragrant alcohol of formula ROH and Y represents a $C_7$ to $C_{24}$ linear or branched, saturated or unsaturated alkyl radical, or a $-(CH_2)_n COOR$ group wherein R is defined as above and n is an integer from 0 to 6; or b. Y represents a $C_7$ to $C_{24}$ linear or branched, saturated or unsaturated alkyl radical and R represents a group of formula

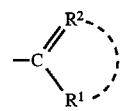

wherein, either $R^1$ represents hydrogen and $R^2$ represents an alkylidene radical derived from a fragrant aldehyde of formula

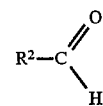

or $R^2$ represents an alkylidene radical and $R^1$ an alkyl radical, $R^1$ and $R^2$ being then derived from an fragrant ketone of formula

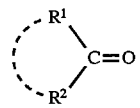

and, optionally, being part of a ring such as indicated by the dotted line which contains 5 to 18 carbon atoms and can be substituted.

The process has the advantage of providing an effect of slow diffusion ("slow release") of said fragrant alcohol, aldehyde or ketone, thus prolonging the odour effect of the latter on fabrics.

18 Claims, No Drawings

PROCESS FOR PERFUMING TEXTILES

TECHNICAL FIELD AND PRIOR ART

The present invention relates to the field of perfumery and, more particularly, to improved perfumed detergents and fabric softeners.

The use of enzymes in fabric detergents, in order to improve their efficiency, has been known for a number of years. Amongst said enzymes, lipases are particularly preferred, as a result of their capacity to hydrolyse the fat materials on the dirty linen and thus to facilitate its cleaning. However, it is known that malodour problems can occasionally occur under certain application conditions. In order to solve these malodour problems, there has been proposed a method (see for example EP 430 315) consisting in carefully choosing the perfuming ingredients incorporated in the detergents and which, following the washing, are deposited on the fabrics. Therefore, appropriate perfuming of said detergents appears to be extremely important.

On the other hand, it would be desirable that said detergents and fabric softeners are able to impart to the fabrics a long-lasting odour, such that the user perceives this odour even a long time after the textiles have been washed and subsequently dried. To this end, it has been known to use in the fabric detergents and softeners perfuming ingredients which have a good tenacity on the fabrics, i.e. ingredients whose odour, once imparted to the textiles upon the washing, can then be perceived by the consumer for several days. However, there are many perfuming substances known for their extremely pleasant odours, and namely a quality of "freshness" often associated with the notion of cleanliness, which substances are unfortunately not very tenacious, or even not tenacious at all, on fabrics, such that their perfuming effect can only be perceived very briefly, at the most for a few hours following the washing and drying operations. Clearly, prolonging the fragrance effect of such substances, and thus the "freshness" of the fabrics, would be highly desirable.

The present invention brings precisely a novel solution to this problem. We have now unexpectedly discovered a better process for perfuming textiles washed with detergents containing lipases. We have in fact been able to establish that, by adding particular ingredients to the fabric detergent and/or to the fabric softener that is subsequently applied, one could distinctly improve the odour of the fabrics treated with these products and prolong in a remarkable way the fragrance of said fabrics after drying.

DESCRIPTION OF THE INVENTION

A first object of the present invention is thus to provide a process for perfuming fabrics washed in the presence of a lipase-containing detergent and, optionally, subsequently treated with a fabric softener, said process being characterized in that said detergent and/or said fabric softener contains a compound of formula

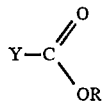

wherein
a. R represents a radical derived from a fragrant alcohol of formula ROH and Y represents a $C_7$ to $C_{24}$ linear or branched, saturated or unsaturated alkyl radical, or a $-(CH_2)_n COOR$ group wherein R is defined as above and n is an integer from 0 to 6; or b. Y represents a $C_7$ to $C_{24}$ linear or branched, saturated or unsaturated alkyl radical and R represents a group of formula

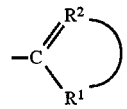

wherein, either $R^1$ represents hydrogen and $R^2$ represents an alkylidene radical derived from a fragrant aldehyde of formula

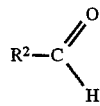

or $R^2$ represents an alkylidene radical and $R^1$ an alkyl radical, $R^1$ and $R^2$ being then derived from a flagrant ketone of formula

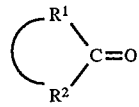

and, optionally, being part of a ring such as indicated by the dotted line which contains 5 to 18 carbon atoms and can be substituted.

By an alkylidene radical derived from a fragrant aldehyde or ketone, it is understood here a radical which, upon the conversion of enol-ester (I) into said aldehyde or ketone, regenerates the corresponding R group which is the substituent of said aldehyde or ketone. Thus, for example, when the flagrant aldehyde is 3,7-dimethyl-6-octenal (R is 3,7-dimethyl-6-octenyl), the corresponding alkylidene radical in enol-ester (I) is 3,7-dimethyl-1,6-octadienyl.

According to a variant of the invention, there is provided a process for perfuming fabrics washed in the presence of a lipase-containing detergent, which process comprises the treatment of said fabrics, after the washing cycle, with a fabric softener containing a compound of formula (I) as defined above.

By "flagrant alcohol", "flagrant aldehyde" or "fragrant ketone" it is meant here any alcohol, aldehyde, respectively ketone, of current use in perfumery, which is capable of imparting an odour to fabrics or textiles, upon the process of washing and/or the treatment with a fabric softener. We have in fact discovered that the perfuming effect of such compounds could be remarkably improved, and namely their diffusion prolonged, if they were replaced by the corresponding compound (I) in the detergent or fabric softener used.

This result is all the more surprising in that the compounds (I) are themselves either devoid of odour, or they possess weak and characterless odours, and are thus apparently useless for perfumery. Yet, when used according to the invention, they are not only capable of imparting to the fabrics the characteristic odour of the corresponding alcohol, aldehyde or ketone, but also of prolonging their effect of diffusion, such that said odour develops itself for much longer periods of time than in the case where said corresponding alcohol, aldehyde or ketone is directly added to the detergents or fabric softeners. Therefore, the use of compounds (I) according to the process of the invention is translated into an enhanced substantivity of the corresponding alcohols, aldehydes and ketones.

The advantages of this process are all the more obvious in the case of the numerous odoriferous alcohols which are known to be weakly tenacious on washed fabrics and the odour of which, although distinctly perceived when the fabrics are removed from the washing machine, does not remain on the linen and can no longer be perceived after 12 to 24 h.

Many examples of such alcohols can be found in the prior art, some of which only contribute to the odour of the fabrics for a very short time, and no doubt many others will be discovered in the future. For all these alcohols, the process according to the invention makes it possible to remarkably improve their odoriferous performance on fabrics, by prolonging the diffusion time of their characteristic notes and thus the time during which they contribute significantly to the overall odour. We have in fact established that the use of the corresponding compounds (I) in the detergents and/or fabric softeners made it possible to obtain a perfuming effect equivalent to the one that would have been observed with the prolonged diffusion ("slow-release") of the alcohol, if such a diffusion would have been possible, which is not the case in practice.

Quite clearly, it is impossible to list in an exhaustive manner all the alcohols of formula ROH known to this day, which are capable of imparting pleasant odours to the textiles treated with the laundry products perfumed by way of said alcohols, and the perfuming effect of which can be remarkably improved according to the invention. However, by way of example, one can cite alcohols such as anisic alcohol, cinnamic alcohol, fenchylic alcohol, 9-decen-1-ol, phenethylol, citronellol, 3-methyl-5-phenyl-1-pentanol (origin: Firmenich SA, Geneva, Switzerland), Mayol® (7-p-menthan-1-ol; origin: Firmenich SA, Geneva, Switzerland), dihydromyrcenol (2,6-dimethyl-7-octen-2-ol), geraniol (3,7-dimethyl-2,6-octadien-1-ol), (Z)-3-hexen-1-ol, 1-hexanol, 2-hexanol, 5-ethyl-2-nonanol, 2,6-nonadien-1-ol, borneol, 1-octen-3-ol, 4-cyclohexyl-2-methyl-2-butanol (origin: Firmenich SA, Geneva, Switzerland), 2-methyl-4-phenyl-2-butanol, 2-methyl-1-phenyl-2-propanol, cyclomethylcitronellol, decanol, dihydroeugenol, 8-p-menthanol, 3,7-dimethyl-1-octanol, 2,6-dimethyl-2-heptanol, dodecanol, eucalyptol, eugenol, Florol® (tetrahydro-2-isobutyl-4-methyl-4(2H)-pyranol; origin: Firmenich SA, Geneva, Switzerland), isoeugenol, linalol, Tarragol® (2-methoxy-4-propyl-1-cylohexanol; origin: Firmenich SA, Geneva, Switzerland), terpineol, tetrahydromuguol, 3,7-dimethyl-3-octanol and Lyral® (3 and 4-(4-hydroxy-4-methylpentyl)-cyclohex-3-ene-1-carbaldehyde: orgin International Flavors and Fragrances, USA).

It is quite obvious, however, that the process of the invention is perfectly general and can relate to many other alcohols which the skilled person is quite able to choose from the general knowledge in the art and as a function of the olfactive effect it desires to achieve.

Analogous considerations apply to the aldehydes of formula

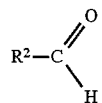

and to the ketones of formula

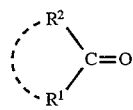

The process of the invention is advantageous whenever the compounds such as those mentioned above show a weak tenacity on fabrics, and there are many odoriferous aldehydes and ketones whose performance on textiles turns out to be disctinctly improved when these compounds exert their perfuming activity by way of the corresponding enol-esters of formula (I).

Again, although one cannot cite in an exhaustive manner all the fragrant aldehydes and ketones which can be used according to the process of the invention, there can be cited, by way of example, compounds such as $C_6$ to $C_{12}$ aldehydes, hydratropic aldehyde, methyl nonyl acetaldehyde, phenylpropanoic aldehyde, Acropal® [3-or 4-(4-methyl-3-pentenyl)-3-cyclohexene-1-carbaldehyde; origin: Givaudan-Roure, Vernier, Switzerland], 2-methyldecanal, 4-isopropyl-1-benzeneacetaldehyde, (4-methyl-1-phenyl)acetaldehyde, Z-6-nonenal, citral, citronellal, 9-decenal, 3-(4-isopropyl-1-phenyl)-2-methylpropanol (origin: Firmenich SA, Geneva, Switzerland), (E,E)-2,4-heptadienal, (E,E)-2,4-nonadienal, (E,E)-2,4-decadienal, 5,9-dimethyl-4,9-decadienal, (Z)-6-octenal, Farenal® (2,6,10-trimethyl-9-undecenal; origin: Givaudan-Roure, Vernier, Switzerland), Foliaver® [3-(4-methoxy-1-phenyl)-2-methylpropanal; origin: International Flavors and Fragrances, USA], Heliopropanal® [3-(1,3-benzodioxol-5-yl)-2-methylpropanal; origin: International Flavors and Fragrances, USA], (Z)-4-heptenal, le 3,5,5-trimethylhexanal (origin: International Flavors and Fragrances, USA), (4-methyl-1-phenoxy)acetaldehyde, hydroxycitronellal, isocyclocitral (origin: International Flavors and Fragrances, USA), Lilial® [3-(4-tert-butyl-1-phenyl)-2-methylpropanal; origin: Givaudan-Roure, Vernier, Switzerland], le 1-p-menthene-9-carbaldehyde (origin: Firmenich SA, Geneva, Switzerland), Lyral® [3-and 4-(4-hydroxy-4-methylpentyl)-3-cyclohexene-1-carbaldehyde; origin: International Flavors and Fragrances, USA], 2,6-dimethyl-5-heptenal, 1-p-menthen-9-al, (E)-2-octenal, (2E,6Z)-2,6-nonadienal, 3-methyl-5-phenylpentanal, (E)-4-decenal, (E)-2-undecenal, 3,7-dimethyloctanal, Zestover (2,4-dimethyl-3-cyclohexene-1-carbaldehyde; origin: Firmenich SA, Geneva, Switzerland), 3-phenylbutanal, Scentenal® (octahydro-5-methoxy-4,7-methano-1H-indene-2-carboxaldehyde; origin: Firmenich SA, Geneva, Switzerland), 2,5,9-trimethyl-4,9-decadienal, Intreleven aldehyde (undecenal; origin: International Flavors and Fragrances, USA), 4-methyl-phenyl-propanoic aldehyde, 4-(4-hydroxy-1-phenyl)-2-butanone, benzylacetone, the ionones, 3-(4-tert-butyl-1-phenyl) propanal, carvone, 3,7-dimethyl-1,1-bis(11-methyldodecyloxy)-2,6-octadiene, muscone, 2-pentyl-1-cyclopentanone, l'ethyl amyl ketone, l'ethyl pentyl ketone, la 2-heptyl-1-cyclopentanone, geranylacetone, Iralia® (methylionone; origin: Firmenich SA, Geneva, Switzerland), Iso E super [1-(octahydro-2,3,8,8-tetramethyl-2-naphtalenyl)-1-ethanone; origin: International Flavors and Fragrances, USA], 6-methyl-5-hepten-2-one, methyl jasmonate, methyl hexyl ketone, methyl pentyl ketone, methylnonyl ketone, cis-jasmone, Hedione® (methyl dihydrojasmonate; origin: Firmenich SA, Geneva, Switzerland), civettone, 4-(1,1-dimethylpropyl)-1-cyclohexanone, Exaltone® (cyclopentadecanone; origin: Firmenich SA, Geneva, Switzerland), 2,6,6-trimethyl-2-cyclohexene-1,4-dione, p-tert-butylcyclohexanone, tricyclo[6.2.1.0$^{2.7}$]undec-9-en-3-one (origin: Firmenich SA, Geneva, Switzerland), 10,10-dimethyltricyclo[7.1.10$^{2.7}$]undec-2-en-4-one (origin: Firmenich SA, Geneva, Switzerland), Vertofix coeur (origine: International Flavors and Fragrances, USA), la perhydro-5,5,8a-trimethyl-2-naphtalenone (origin: Firmenich SA, Geneva, Switzerland) or 5-methyl-exo-tricyclo[6.2.1.0$^{2.7}$] undecan-4-one.

Furthermore, it should be noted that the process of the invention is of much more general use than merely the improved perfuming of textiles treated with laundry products containing lipases. It constitutes, in fact, a general process for washing said textiles which is also advantageous whenever it is desired to improve the activity of certain agents, fragrant or other, currently present in laundry products, i.e. detergents and fabric softeners. It is well-known for instance that said laundry products are often very aggressive media, wherein a great number of perfuming ingredients, and more particularly fragrant aldehydes, turn out to be unstable and cannot therefore be used to perfume those products, nor the textiles washed therewith. The use according to the invention of the corresponding esters and enol-esters of formula (I) can obviate this problem whenever said enol-esters turn out to be more stable. It is also quite clear that one can make use of the process of the invention to improve and prolong the action of bactericide agents, namely alcohols, whether they are flagrant or not.

Therefore, the process according to the invention is in fact a general process for treating textiles or fabrics upon the washing of the latter with a lipase-containing detergent, which washing can be followed by treatment with a fabric softener, according to which process any alcohol, aldehyde or ketone currently used in fabric detergents or softeners for its perfuming, bactericide or other activity, can be replaced by the corresponding compound (I), so as to improve its activity.

Compounds (I) are novel chemical entities and thus are also the object of the invention. Amongst said compounds, those wherein Y represents a $C_7$ to $C_{24}$ linear or branched, saturated or unsaturated alkyl radical are fatty acids esters or enol-esters which do not themselves possess an interesting odour, but which, when used according to the process of the invention, are capable of imparting to the fabrics the fragrances typical of the corresponding alcohols, aldehydes and ketones defined above. Said compounds, in particular the derivatives having 12 to 16 carbon atoms, are preferred according to the invention, owing to the particularly advantageous results obtain upon their use.

As regards the compounds (I) wherein Y represents a —$(CH_2)_n$COOR group, R being defined as above and n being an integer from 0 to 6, they are novel diesters, which are either-devoid of odour, or possess odours which are not particularly useful for perfumery. However, they showed similar behaviour to that of the compounds (I) cited hereabove, when used in the context of the present invention.

The compounds (I) of the invention can be added to the detergents and fabric softeners either on their own, or in admixture with other perfuming ingredients, solvents or adjuvants, of current use in perfumery. The concentrations in which they can be added to the detergents and fabric softeners according to the invention have the values usual in the art for this type of products. The skilled person is quite able to select such values as a function of the nature of the product to be perfumed and of the desired olfactive effect. By way of example, concentrations of the order of 0.01 to 1%, or even up to 5%, by weight of compound (I), relative to the weight of detergent or fabric softener composition, can be cited.

The fabric detergents and softeners according to the invention can take the form of powders or granular solids, bars, pastes or yet aqueous or non-aqueous liquids, and contain the usual ingredients for this type of product. Thus, the detergents can typically contain, in addition to the lipase (see, for example, EP 430 315 for a detailed description of the type of lipases that can be used according to the present invention), for example active anionic, cationic, zwitterionic or non-ionic compounds, as well as filling agents, bleaching agents, confining agents and other ingredients of current use in the detergent bases intended for washing linen. A detailed description of the base detergent compositions which are adapted to be used according to the process of the invention is unwarranted here. A great many examples of such compositions can be found in the art and namely in the literature which is cited for instance in the European patent application mentioned above, or yet in European patent application EP 397 245. By way of example, a base detergent of this type, to which there is added the lipase in the desired concentration, can have the following composition (origin: Henkel KGaA, Düsseldorf, Germany):

| Ingredients | % by weight |
|---|---|
| Linear sodium alkyl benzene sulfonate (average length of the alcane chain: $C_{11.5}$) | 8.0 |
| Ethoxylated tallow alcohol (14 EO) | 2.9 |
| Sodium soap (chain length $C_{12-16}$:13–26% $C_{18-22}$:74–87%) | 3.5 |
| Sodium triphosphate | 43.8 |
| Sodium silicate ($SiO_2$:$Na_2O$ = 3.3:1) | 7.5 |
| Magnesium silicate | 1.9 |
| Carboxymethylcellulose | 1.2 |
| Sodium ethylenediaminetetraacetate | 0.2 |
| Sodium sulfate | 21.2 |
| Water | 9.8 |
| Total | 100.0 |

Similar considerations apply to the fabric softener bases according to the invention, which will typically contain cationic softening ingredients of the type cited in EP 397 245 or in the literature mentioned in this reference.

The compounds of the invention can be prepared by conventional synthetic methods. For example, the derivatives of fragrant alcohols were prepared by the esterification method summarized in the following reaction scheme:

Scheme I

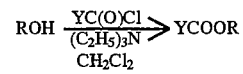

wherein Y and R are defined as in claim 1.

The enol-esters of fragrant aldehydes and ketones were also prepared by conventional methods, starting from said aldehydes and ketones, by way of reactions of the type of those represented hereinafter:

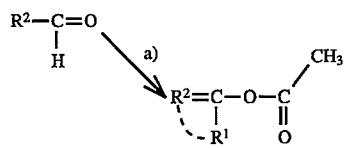

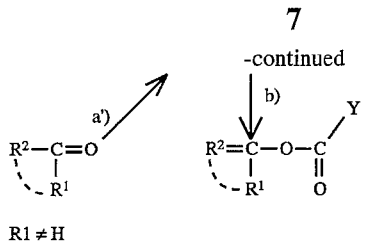

R¹ ≠ H

R¹, R² and Y are defined as in claim 1b.

a) acetic anhydride; potassium acetate; ethylamine; 120°; see, for example, D. P. Simmons et al., Helv. Chim. Acta 71, 1000 (1988)

a') acetic anhydride; p-toluenesulfonic acid (cat.); 120°; see, for example, T. Taapken et al., J. Chem. Soc. Perkin Trans. I, 1994, 1439 b) potassium tert-butoxyde; YCOCl; see, for example, P. Duhamel et al., J. Chem. Soc. Perkin Trans. I, 1993, 2509

The reaction conditions are described in detail in the preparation examples presented hereinafter, wherein the temperatures are in degrees centigrade and the abbreviations have the usual meaning in the art. The invention will also be illustrated by way of application examples.

EMBODIMENTS OF THE INVENTION

Example 1

Preparation of Mono-esters
General Method

To a stirred solution of the appropriate ROH alcohol (0.064 mole) and triethylamine (7.4 g, 0.073 mole) in $CH_2Cl_2$ (110 ml), there was added dropwise during 20 min, at 15° and under $N_2$ the corresponding YC(O)Cl acyl chloride (0.07 mole), wherein Y is a $C_7$ to $C_{24}$, linear of branched, saturated or unsaturated alkyl radical. After 2 h at room temperature, the mixture was poured on aq. sat. $NaHCO_3$ (excess) and the organic phase was separated. Extraction of the aqueous phase with $CH_2Cl_2$ was followed by washing of the combined organic phases with 10% aqueous NaCl. The reaction product was dried over $Na_2SO_4$, concentrated and distilled to provide the desired ester in a pure state and in 80 to 90% yield.

The following mono-esters were prepared according to the above-described general method.

a. 2-phenylethyl octanoate
B.p. 100°–101°/4 Pa
IR($CHCl_3$): 2930, 2858, 1728, 1498, 1455, 1168, 1106 cm$^{-1}$
NMR($^1$H, 360 MHz): 0.88(t, J=7 Hz, 3H); 1.27(8H); 1.59(2H); 2.28(t, J=7 Hz, 2H); 2.93(t, J=7 Hz, 2H); 4.29(t, J=7 Hz, 2H) 7.20–7.35(5H) δ ppm.
NMR($^{13}$C): 173.7(s); 138.0(s); 128.9(d); 128.5(d); 126.5 (d); 64.7(t); 35.2(t); 34.4(t); 31.7(t); 29.1(t); 28.9(0; 25.0(t); 22.6(t); 14.0(q) δ ppm.
MS: 248(0, M$^+$), 127(2), 104(100), 57(12).

b. 2-phenylethyl hexadecanoate
M.p. 40°
IR($CHCl_3$): 2927, 2855, 1728, 1456, 1174 cm$^{-1}$
NMR($^1$H, 360 MHz): 0.88(t, J=7 Hz, 3H); 1.26(24H); 1.58(2H); 2.27(t, J=7 Hz, 2H); 2.93(t, J=7 Hz, 2H); 4.29(t, J=7 Hz, 2H); 7.20–7.35(5H) δ ppm.
NMR($^{13}$C): 173.7(s); 138.0(s); 128.9(d); 128.5(d); 126.5 (d); 64.7(t); 35.3(t); 34.4(t); 32.0(t); 29.7(2t); 29.5(t); 29.4 (t); 29.3(t); 29.2(t); 25.0(t); 22.7(t); 0;14.1(q) δ ppm.
MS: 360(0, M$^+$), 104(100).

c. 3,7-dimethyl-6-octenyl octanoate
B.p. 108°–109°/2.7 Pa
IR($CHCl_3$): 2829, 2858, 1725, 1460, 1379, 1231, 1171, 1106 cm$^{-1}$
NMR($^1$H, 360 MHz): 0.88(t, J=7 Hz, 3H); 0.91(d, J=7 Hz, 3H); -1.10–1.80(15H); 1.61(s, 3H); 1.68(s, 3H); 1.98(m, 2H); 2.29(t, J=7 Hz, 2H 4.10(m, 2H); 5.09(broad t, J=7 Hz, 1H) δ ppm.
NMR($^{13}$C): 173.9(s); 131.3(s); 124.7(d); 62.8(t); 37.1(t); 35.6(t); 34.5(t); 31.7(0; 29.6(d); 29.2(t); 29.0(t); 25.7(q); 25.5(0; 25.1(t); 22.6(t); 19.5(q); 17.7(q); 14.1(q) δ ppm.
MS: 282(0, M$^+$), 138(30), 123(56), 109(25), 95(77), 81(100), 69(59)

d. 3,7-dimethyl-6-octenyl hexadecanoate
B.p. (bulb-to-bulb distillation) 210°–230°/5.3 Pa
IR($CHCl_3$): 2827, 2855, 1725, 1465, 1233, 1178 cm$^{-1}$
NMR($^1$H, 360 MHz): 0.88(t, J=7H, 3H); 0.92(d, J=7 Hz, 3H); 1.15–1.35(26H); 1.44(m, 1H); 1.60(s, 3H); 1.68(s, 3H); 1.50–1.70(4H); 1.98(m, 21H); 2.28(t, J=7 Hz, 2H); 4.10(m, 2H); 5.09(broad t, J=7 Hz, 1H) δ ppm.
NMR($^{13}$C): 173.9(s); 131.3(s); 124.6(d); 62.8(t); 37.1(t); 35.6(t); 34.5(t); 32.0(t); 0;29.7(2t); 29.6(d); 29.5(t); (0;29.4 (t); 29.3; (0;29.2(t); 25.7(q); 25.5(t); 0;25.1(22.7(t); 19.5(q); 17.7(q); 14.1(q) δ ppm.
MS: 394(0, M$^+$), 138(32), 123(30), 95(60), 82(70), 69(70), 57(100).

e. 3-methyl-5-phenylpentyl octanoate
B.p. 133°–135°/2.7 Pa
IR($CHCl_3$): 2930, 2858, 1728, 1496, 1456, 1231, 1171, 1106 cm$^{-1}$
NMR($^1$H, 360 MHz): 0.88(t, J=7 Hz, 3H); 0.98(d, J=7 Hz, 3H); 1.28(8H); 1.40–1.80(7H); 2.27(t, J=7 Hz, 2H); 2.62(m, 2H); 4.11(m, 2H); 7.10–7.30(5H) δ ppm.
NMR($^{13}$C): 173.9(s); 142.7(s); 128.3(2d); 125.7(d); 62.6 (t); 38.8(t); 35.5(t); 34.4(t); 33.3(t); 31.7(t); 29.6(d); 29.2(t); 29.0(t); 25.0(t); 22.6(t); 19.5(q); 14.1(q) δ ppm.
MS: 304(0, M$^+$), 160(55), 131(30), 104(100), 91(56).

f. 3-methyl-5-phenylpentyl hexadecanoate
B.p. (bulb-to-bulb distillation) 250°/4 Pa
IR(CHCl³): 2927, 2855, 1727, 1456, 1235, 1178 cm$^{-1}$
NMR($^1$H, 360 MHz): 0.88(t, J=7 Hz, 3H); 0.97(d, J=7 Hz, 3H); 1.26(24H); 1.48(2H); 1.55–1.80(5H); 2.27(t, J=7 Hz, 2H); 2.62(m, 2H); 4.10(m, 2H); 7.15–7.30(5H) δ ppm.
NMR($^{13}$C): 173.9(s); 142.6(s); 128.3(2d); 125.7(d); 62.6 (t); 38.8(t); 35.5(t); 34.5(t); 33.3(t); 32.0(t); 29.7(2t); 29.7 (d); 29.6(t); 29.5(t); 29.4(t); 29.3(t); 29.2(t); 25.1(22.7(t); 19.5(q); 14.1(q) δ ppm.
MS: 416(0, M$^+$), 160(43), 129(22), 115(36), 104(72), 91(68), 71(61), 57(100).

g. 7-p-menthanyl octanoate (cis/trans 70:30)
B.p. 105°–115°/2.7 Pa
IR($CHCl_3$): 2929, 2858, 1724, 1453, 1232, 1172, 1106 cm$^{-1}$
NMR($^1$H, 360 MHz): cis-7: 0.86(d, J=7 Hz, 6H); 0.88(t, J=7 Hz, 6H); 2.30(t, J=7 Hz, 2H); 4.02(d, J=7 Hz, 2H) δ ppm.
trans-7: 2.30(t, J=7 Hz, 2H); 3.88(d, J=7 Hz, 2H) δ ppm.
NMR($^{13}$C): cis-7: 174.0(s); 66.6(t); 43.0(d); 34.5(33.9(d); 30.6(d); 29.9(t); 29.2(t); 29.1(t); 26.5(t); 25.6(t); 25.1(t); 20.3(q); 14.0(q) δ ppm.
trans-7: 174.0(s); 69.5(t); 44.1(d); 37.5(t); 32.9(d); 31.7 (t); 22.6(t); 19.8(q); 14.0(q) δ ppm.
MS: cis-7: 282(0, M$^+$), 138(23), 123(17), 109(35), 95(100), 81(27). trans-7: 282(0, M$^+$), 138(27), 123(17), 109(22), 95(100), 81(35).

h. 9-decenyl octanoate

B.p. 120°–121°/2.7 Pa
IR(CHCl$_3$): 2830, 2857, 1725, 1466, 1171 cm$^{-1}$
NMR($^1$H, 360 MHz): 0.88(t, J=7 Hz, 3H); 1.30(18H); 1.61(4H); 2.04(broad q, J=7 Hz, 2H); 2.29(t, J=7 Hz, 2H); 4.06(t, J=7 Hz, 2H); 4.93(broad d, J=11 Hz, 1H); 4.99(broad d, J=17 Hz, 1H); 5.80(m, 1H) δ ppm.
NMR($^{13}$C): 173.9(s); 139.1(d); 114.2(t) 64.4(t); 34.5(t); 33.8(t); 31.8(t); 29.4(t); 29.3(t); 29.2(t); 29.1(t); 29.0(2t); 28.8(t); 26.0(t); 25.1(t); 22.7(t); 14.1(q) δ ppm.
MS: 282(0, M$^+$), 145(38), 109(38), 96(86), 82(89), 68(91), 55(100).

i. 9-decenyl nonanoate
B.p. (bulb-to-bulb distillation) 130°–160°/2.7 Pa
NMR($^1$H, 360 MHz): 0.88(t, J=7 Hz, 3H); 1.20–1.45 (20H); 1.61(4H); 2.04 (broad q, J=7 Hz, 2H); 2.29(t, J=7 Hz, 2H); 4.06(t, J=7 Hz, 2H); 4.93(broad d, J=11 Hz, 1H); 4.99(broad d, J=17 Hz, 1H); 5.80(m, 1H) δ ppm.
NMR($^{13}$C): 174.0(s); 139.1(d); 114.2(t); 64.4(t); 34.5(t) 33.8(t); 31.9(t); 29.4(t); 29.3(t); 29.2(2t); 29.1(t); 29.0(t); 28.7(t); 26.0(t); 25.1(t); 22.7(t); 14.1(q) δ ppm.
MS: 296(0, M$^+$), 159(27), 138(28), 96(100), 82(75), 68(73), 55(83).

j. 9-decenyl decanoate
B.p. 144°–145°/2.7 Pa
IR(CHCl$_3$): 2929, 2856 1726, 1466, 1178 cm$^{-1}$
NMR($^1$H, 360 MHz): 0.88(t, J=7 Hz, 3H); 1.30(22H); 1.61(4H); 2.04(broad q, J=7 Hz, 2H); 2.29(t, J=7 Hz, 2H); 4.05(t, J=7 Hz, 2H); 4.93(broad d, J=11 Hz, 1H); 4.98broad d, J=17 Hz, 1H; 5.80(m, 1H) δ ppm.
NMR($^{13}$C): 173.9(s); 139.1(d); 114.2(t); 64.4(t); 34.5(t); 33.8(t); 31.9(t); 29.5(t); 29.3(t); 29.2(t); 29.1(t); 29.0(t); 28.7(t); 26.0(t); 25.1(t); 22.7(t); 14.1(q) δ ppm.
MS: 310(0, M$^+$), 138(33), 109(29), 96(100), 82(82), 68(98).

k. 9-decenyl undecanoate
B.p. (bulb-to-bulb distillation) 130°–150°/20 Pa
NMR($^1$H, 360 MHz): 0.88(t, J=7 Hz, 3H); 1.20–1.45 (24H); 1.61(4H); 2.04(broad q, J=7 Hz, 2H); 2.29(t, J=7 Hz, 2H); 4.06(t, J=7 Hz, 2H); 4.93(broad d, J=11 Hz, 1H); 4.99(broad d, J=17 Hz, 1H); 5.81(m, 1H) δ ppm.
NMR($^{13}$C): 173.9(s); 139.1(d); 114.2(t); 64.4(t); 34.5(t); 33.8(t); 32.0(t); 29.6(2t); 29.4(2t); 29.3(t); 29.1(t); 29.0(t); 28.8(t); 26.0(t); 25.1(t); 22.7(t); 14.1(q) δ ppm.
MS: 324(0, M$^+$), 187(20), 138(43), 109(33), 96(100), 82(96), 68(89), 55(91).

l. 9-decenyl dodecanoate
B.p. 164°–165°/4 Pa
IR(CHCl$_3$): 2928, 2856, 1726, 1216 cm$^{-1}$
NMR($^1$H, 360 MHz): 0.89(t, J=7 Hz, 3H); 1.28(26H); 1.62(4H); 2.04(broad q, J=7 Hz, 2H); 2.29(t, J=7 Hz, 2H); 4.06(t, J=7 Hz, 2H); 4.93(broad d, J=11 Hz, 1H); 4.98(broad d, J=17 Hz, 1H; 5.80(m, 1H) δ ppm.
NMR($^{13}$C): 174.0(s); 139.2(d); 114.2(t); 64.4(t); 34.5(t); 33.8(t); 32.0(t); 29.6(t); 29.5(t); 29.4(2t); 29.3(t); 29.2(t); 29.1(2t); 28.9(t); 28.7(t); 26.0(t); 25.1(t); 22.7(t); 14.1(q) δ ppm.
MS: 338(0, M$^+$), 138(48), 109(35), 96(100), 82(96), 68(89), 55(98).

m. 9-decenyl tridecanoate
B.p. (bulb-to-bulb distillation) 150°–175°/13 Pa
NMR($^1$H, 360 MHz): 0.88(t, J=7 Hz, 3H); 1.20–1.45 (28H); 1.61(4H); 2.04(broad q, J=7 Hz, 2H); 2.29(t, J=7 Hz, 2H); 4.05(t, J=7 Hz, 2H); 4.93(broad d, J=11 Hz, 1H); 4.99(broad d, J=17 Hz, 1H); 5.81(m, 1H) δ ppm.
NMR($^{13}$C): 174.0(s); 139.1(d); 114.2(t); 64.4(t); 34.5(t); 33.8(t); 32.0(t); 29.5(t); 29.4(t); 29.3(t); 29.2(t); 29.1(t); 29.0(t); 28.7(t); 26.0(t); 25.1(t); 22.7(t); 14.1(q) δ ppm.
MS: 352(0, M$^+$), 138(52), 110(41), 96(99), 82(83), 68(93), 55(100).

n. 9-decenyl tétradecanoate
B.p. (bulb-to-bulb distillation) 200°–220°/4 Pa
NMR($^1$H, 360 MHz): 0.88(t, J=7 Hz, 3H); 1.28(30H); 1.62(4H); 2.04(broad q, J=7 Hz, 2H); 2.29(t, J=7 Hz, 2H); 4.06(t, J=7 Hz, 2H); 4.93(broad d, J=11 Hz, 1H); 4.99(broad d, J=17 Hz, 1H; 5.81(m, 1H) δ ppm.
NMR($^{13}$C): 174.0(s); 139.1(d); 114.2(t); 64.4(t); 34.5(t); 34.5(t); 33.8(t); 32.0(t); 29.7(t); 29.5(t); 29.4(t); 29.3(2t); 29.2(t); 29.1(t); 29.0(t); 28.7(t); 26.0(t); 25.1(t); 22.7(t); 14.1(q) δ ppm.
MS: 366(0, M$^+$), 138(52), 110(47), 96(100), 82(96), 55(96).

o. 9-decenyl pentadecanoate
B.p. (bulb-to-bulb distillation) 175°–210°/13 Pa
NMR($^1$H, 360 MHz): 0.88(t, J=7 Hz, 3H); 1.20–1.45 (32H); 1.62(4H); 2.04(broad q, J=7 Hz, 2H); 2.29(t, J=7 Hz, 2H); 4.06(t, J=7 Hz, 2H); 4.93(broad d, J=11 Hz, 1H; 4.99(broad d, J=17 Hz, 1H); 5.81(m, 1H) δ ppm.
NMR($^{13}$C): 174.0(s); 139.1(d); 114.2(t); 64.4(t); 34.5(t); 33.8(t); 32.0(t); 29.7(2t); 29.5(t); 29.4(t); 29.3(t); 29.2(t); 29.1(t); 29.0(t); 29.0(t); 28.7(t); 26.0(t); 25.1(t); 22.7(t); 14.1(q) δ ppm.
MS: 380(0, M$^+$), 138(50), 110(30), 96(100), 82(85), 68(79), 55(80).

p. 9-decenyl hexadecanoate
NMR($^1$H, 360 MHz): 5.84(m, 1H); 4.95(m, 2H); 4.05(t, 2H); 3.73(q, 4H); 2.31(t, 2H); 2.05broad q, 2H); 1.61(m, 4H); 1.2–1.4(broad m, 30H); 0.89(m, 3H) δ ppm.
NMR($^{13}$C): 14.12(q); 18.44(q); 22.72(t); 25.06(t); 25.95 (t); 28.68(t); 28.92(t); 29.05(t); 29.21(t); 29.30(t); 29.39(t); 29.51(t); 29.64(t); 29.71(t); 31.95(t); 33.80(t); 34.45(t); 58.45(t); 64.41(t); 114.17(t); 139.16(d); 174.07(s) δ ppm.
MS: 394(0, M$^+$), 96(72), 83(70), 82(88), 55(100).

q. 1-methylpentyl hexadecanoate
NMR($^1$H, 360 MHz): 4.90(m, 1H); 2.26(t, 2H); 1.65(m, 4H); 1.25–1.32(m, 28H); 1.20(d, 3H); 0.89(q, 6H) δ ppm.
NMR($^{13}$C): 13.97(q); 14.00(q); 20.40(q); 22.56(t); 22.7 (t); 25.1(t); 27.6(t); 29.2(t); 29.3(t); 29.4(t); 29.5(t); 29.6(t); 29.7(t); 29.73(t); 31.97(t); 34.83(t); 35.75(t); 70.74(d); 173.50(s) δ ppm.
MS: 84(100), 69(50), 57(70), 55(62), 43(98).

r. 7-p-menthanyl hexadecanoate
NMR($^1$H, 360 MHz): 0.80–0.95(m, 9H); 1.2–2.0(broad m, 37H); 2.32(t, 2H); 3.88 et 4.02(d, 2H) δ ppm.
NMR($^{13}$C): 14.09(t); 19.8(t); 20.2(t); 22.7(t); 25.12(t); 22.56(t); 26.44(t); 29.10(t); 29.22(t); 29.30(t); 29.38(t); 29.51(t); 29.63(t); 29.71(t); 29.92(t); 30.54(d); 31.97(t); 32.90(d); 33.90(d); 34.50(t); 37.50(d); 42.98(d); 44.11(d); 66.62(t); 69.50(t); 174.05(s) δ ppm.
MS: 93(70), 77(33), 69(100), 43(48), 41(92).

s. hexyl hexadecanoate
NMR($^1$H, 360 MHz): 4.02(t, 2H); 3.86(broad q, 2H); 2.29(t, 2H); 1.60(broad m, 4H); 1.2–1.4(broad m, 28H); 0.90(m, 6H) δ ppm.
NMR($^{13}$C): 14.1(q); 13.97(q); 22.58(t); 22.74(t); 25.11(t); 25.68(t); 28.75(t); 29.24(t); 29.34(t); 29.41(t); 29.54(t); 29.67(t); 29.72(t); 29.74(t); 31.51(t); 32.00(t); 34.50(t); 58.42(t); 64.46(t); 174.07(s) δ ppm.
MS: 340(2, M$^+$), 84(100), 57(55), 56(58), 43(80).

t. (Z)-3-hexenyl hexadecanoate
NMR($^1$H, 360 MHz): 5.45(m, 1H); 5.26(m, 1H); 4(t, 2H); 3.42(s, 4H); 2.2–3.3(m, 8H); 2.0(m, 1H); 1.6(m, 8H); 1.2 (broad m, 30H); 0.8–1.0(m, 6H) δ ppm.
NMR($^{13}$C): 14.14(q); 14.24(q); 20.63(t); 22.73(t); 25.02 (t); 25.59(t); 26.37(t); 26.72(t); 26.82(t); 29.20(t); 29.32(t);

29.40(t); 29.51(t); 29.73(t); 31.97(t); 34.39(t); 93.77(t); 123.83(d); 134.50(d); 173.93(s) δ ppm.

MS: 83(25), 82(100), 67(38), 55(27), 43(14).

u. (E)-3,7-dimethyl-2,6 octadienyl hexadecanoate

NMR($^1$H, 360 MHz): 0.87(t, 3H); 1.26(m, 26H); 1.6(s, 3H); 1.68(s, 3H); 1.70(s, 3H); 2.0–2.15(m, 4H); 2.30(t, 2H); 4.6(d, 2H); 5.09(t, 1H); 5.35(t, 1H) δ ppm.

NMR($^{13}$C): 14.12(q); 16.48(q); 17.69(q); 27.73(t); 25.08(t); 25.68(t); 26.38(t); 29.22(t); 29.33(t); 29.41(t); 29.53(t); 29.67(t); 29.72(t); 31.99(t); 34.45(t); 35.59(t); 61.19(t); 116.60(d); 123.85(d); 131.80(s); 142.06(s); 173.91(s) δ ppm.

MS: 392(0, M$^+$), 93(94), 69(100), 43(89), 41(70).

Example 2

Preparation de di-esters

General Method

The same method as that described in Example 1 was used, but employing half the molar amounts of the corresponding diacyl dichloride [(CH$_2$)$_n$[C(O)Cl]$_2$, n=0 to 6].

The following di-esters were prepared according to this general method:

a. bis(9-decenyl) oxalate

B.p. (bulb-to-bulb distillation): 200°/40 Pa

IR(CHCl$_3$): 2930, 2860, 1770, 1740, 1460, 1312, 1175, 912 cm$^{-1}$

NMR($^1$H, 360 MHz): 1.25–1.45(20H); 1.74(m, 4H); 2.04broad q, J=7 Hz, 4H); 4.28(t, J=7 Hz, 4H); 4.93(broad d, J=11 Hz, 2H); 4.99broad d, J=17 Hz, 2H); 5.80(m, 2H) δ ppm.

NMR($^{13}$C): 158.1(s); 139.0(d); 114.2(t); 67.1(t); 33.8(t); 29.3(t); 29.1(t); 29.0(t); 28.9(t); 28.3(t); 25.7(t) δ ppm.

MS: 366(0, M$^+$), 138(9), 109(13), 96(27), 83(55), 69(45), 55(100).

b. bis(9-decenyl) malonate

B.p. (bulb-to-bulb distillation): 210°/40 Pa

IR(CHCl$_3$): 2940, 2862, 1740, 1465, 1336, 1276, 1155, 915 cm$^{-1}$

NMR($^1$H, 360 MHz): 1.25–1.45(20H); 1.64(m, 4H); 2.04 (broad q, J=7 Hz, 4H); 3.37(s, 2H); 4.14(t, J=7 Hz, 4H); 4.93(broad d, J=11 Hz, 2H); 4.99 (broad d, J=17 Hz, 2H); 5.81(m, 2H) δ ppm.

NMR($^{13}$C): 166.6(s); 139.1(d); 114.2(t); 65.6(t); 41.7(t); 33.8(t); 29.4(t); 29.2(t); 29.1(t); 28.9(t); 28.5(t); 25.8δ ppm.

MS: 380(0, M$^+$), 138(25), 109(21), 105(42), 96(60), 83(100), 68(65), 55(95).

c. bis(9-decenyl) butanedioate

IR(CHCl$_3$): 2935, 2860, 1735, 1460, 1160, 995, 910 cm$^{-1}$

NMR($^1$H, 360 MHz): 1.25–1.45(20H); 1.63(m, 4H); 2.04 (broad q, J=7 Hz, 4H); 2.62(s, 4H); 4.08(t, J=7 Hz, 4H); 4.93(broad d, J=11 Hz, 2H); 4.99broad d, J=17 Hz, 2H); 5.81(m, 2H) δ ppm.

NMR($^{13}$C): 172.3(s); 139.1(d); 114.2(t); 64.9(t); 33.8(t); 29.4(t); 29.3(t); 29.2(t); 29.1(t); 28.9(t); 28.7(t); 25.9(t)δ ppm.

MS: 394(0, M$^+$), 138(10), 119(22), 101(60), 97(38), 83(100), 69(44), 55(76).

d. bis(9-decenyl) pentanedioate

IR(CHCl$_3$): 2940, 2880, 1740, 1464, 1180, 1000, 918 cm$^{-1}$

NMR($^1$H, 360 MHz): 1.25–1.45(20H); 1.62(m, 4H); 1.95 (t, J=7,7 Hz, 2H); 2.04(broad q, J=7 Hz, 4H); 2.37(t, J=7 Hz, 4H); 4.06(t, J=7 Hz, 4H); 4.93(broad d, J=11 Hz, 2H); 4.99(broad d, J=17 Hz, 2H); 5.81(m, 2H) δ ppm.

NMR$^{13}$C): 173.0(s); 139.1(d); 114.2(t); 64.6(t); 33.8(t); 33.4(t); 29.4(t); 29.2(t); 29.1(t); 28.9(t); 28.7(t); 25.9(t) δ ppm.

MS: 408(0, M$^+$), 115(100), 97(14), 87(20), 83(26), 69(19), 55(39).

e. bis(9-decenyl) hexanedioate

IR(CHCl$_3$): 2942, 2864, 1740, 1466, 1180, 1000, 918 cm$^{-1}$

NMR($^1$H, 360 MHz): 1.25–1.45(20H); 1.55–1.75(8H); 2.04broad q, J=7 Hz, 4H); 2.32(m, 4H); 4.06(t, J=7 Hz, 4H); 4.93(broad d, J=11 Hz, 2H); 4.99(broad d, J=17 Hz, 2H); 5.81(m, 2H) δ ppm.

NMR($^{13}$C): 173.4(s); 139.1(d); 114.2(t); 64.5(t); 34.0(t); 33.8(t); 29.4(t); 29.2(t); 29.0(t); 28.9(t); 28.7(t); 25.9(t); 24.5(t) δ ppm.

MS: 422(0, M$^+$), 129(90), 111(64), 101(31), 95(23), 83(60), 67(41), 55(100).

f. (E,E)-bis(3,7-dimethyl-2,6-octadienyl) oxalate

IR(CHCl$_3$): 2929, 1740, 1449, 1378, 1302, 1168 cm$^{-1}$

NMR($^1$H, 360 MHz): 1.60(s, 6H); 1.68(s, 6H); 1.75(s, 6H); 2.09(8H); 4.80(d, J=7 Hz, 4H); 5.07(m, 2H); 5.41 (broad t, J=7 Hz, 2H) δ ppm.

NMR($^{13}$C): 158.0(s); 144.3(s); 132.0(s); 123.6(d) 116.9 (d); 63.8(t); 39.6(t); 26.2(t); 25.7(q); 17.7(q); 16.6(q) δ ppm.

MS: 362(0, M$^+$), 135(7), 93(20), 81(29), 69(100).

g. (E,E)-bis(3,7-dimethyl-2,6-octadienyl) malonate

IR(CHCl$_3$): 2930, 1728, 1447, 1379, 1278, 1149, 983 cm$^{-1}$

NMR($^1$H, 360 MHz): 1.60(s, 6H); 1.69(s, 6H); 1.71(s, 6H); 2.08(8H); 3.38(s, 2H); 4.65(d, J=7 Hz, 4H); 5.08(m, 2H); 5.34(broad t, J=7 Hz, 2H) δ ppm.

NMR($^{13}$C): 166.6(s); 142.9(s); 131.9(s); 123.7(d); 117.8 (d); 62.4(t); 41.7(t); 39.6(t); 26.4(t); 25.7(q); 17.7(q); 16.5 (q) δ ppm.

MS: 376(0, M$^+$), 136(17), 121(15), 93(39), 81(33), 69(100).

h. (E,E)-bis(3,7-dimethyl-2,6-octadienyl) butanedioate

IR(CHCl$_3$): 2930, 1729, 1446, 1384, 1231, 1162 cm$^{-1}$

NMR($^1$H, 360 MHz): 1.61(s, 6H); 1.69(s, 6H); 1.70(s, 6H); 2.08(8H); 2.64(s, 4H); 4.62(d, J=7 Hz, 4H); 5.08(m, 2H); 5.34(broad t, J=7 Hz, 2H) δ ppm.

NMR($^{13}$C): 172.3(s); 142.3(s); 131.8(s); 123.8(d); 118.3 (d); 61.7(t); 39.6(t); 29.3(t); 26.4(t); 25.7(q); 17.7(q) 16.5 (q); δ ppm.

MS: 390(0, M$^+$), 136(17), 121(19), 93(62), 81(27), 69(100).

i. (E,E)-bis(3,7-dimethyl-2,6-octadienyl) pentanedioate

IR(CHCl$_3$): 2930, 1727, 1450, 1232, 1176 cm$^1$

NMR($^1$H, 360 MHz): 1.61(s, 6H); 1.68(s, 6H); 1.70(s, 6H); 1.96(m, 2H); 2.07(8H); 2.37(t, J=7 Hz, 4H), 4.59(d, J=7 Hz, 4H); 5.08(m, 2H); 5.33(broad t, J=7 Hz, 2H) δ ppm.

NMR($^{13}$C): 172.9(s); 142.2(s); 131.8(s); 123.8(d); 118.4 (d); 61.4(t); 39.6(t); 33.4(t); 26.3(t); 25.7(q); 20.3(t); 17.7 (q); 16.5(q) δ ppm.

MS: 404(0, M$^+$), 136(20), 121(18), 93(55), 81(48), 69(100).

j. (E,E)-bis(3,7-dimethyl-2,6-octadienyl) hexanedioate

IR(CHCl$_3$); 2931, 1727, 1446, 1384, 1233, 1174 cm$^1$

NMR($^1$H, 360 MHz): 1.60(s, 6H); 1.68(4H); 1.68(s, 6H); 1.70(6H); 2.07(8H), 2.33(4H); 4.59(d, J=7 Hz, 4H); 5.08(m, 2H); 5.33(broad t, J=7 Hz, 2H) δ ppm.

NMR($^{13}$C): 173.3(s); 142.2(s); 131.8(s); 123.8(d); 118.4 (d); 61.3(t); 39.8(t); 34.0(t); 26.4(t); 25.7(q); 24.5(t); 17.7 (q); 16.5(q) δ ppm.

MS: 418(0, M$^+$), 135(15), 121(15), 93(52), 81(32), 69(100).

5,649,979

Example 3
Preparation of enol-esters
General Method

A 500 ml three-neck flask under argon was charged with 0.162 mole of the appropriate aldehyde of formula

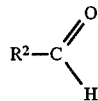

2.5 g (26 mmole) of anhydrous potassium acetate, 34.45 g (0.34 mole) of triethylamine and 250 ml of acetic anhydride. After heating for 6 h at 120°, the reaction mixture was cooled to room temperature, poured on ice, extracted Tree times with petroleum ether 30°–500°, washed 6 times with 100 m of saturated $NaHCO_3$, then with water to neutrality. After drying over $Na_2SO_4$, filtering, concentrating under vacuum and distilling on a Vigreux column, there was obtained the enolacetate corresponding to the starting aldehyde, in the form of a mixture of E and Z isomers. The latter were then separated by preparative gas chromatography. When starting from a ketone of formula

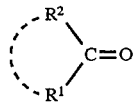

there was followed a method analogous to that described by T. Taapken et al. J. Chem. Soc. Perkin Trans. I, 1994, 1439, wherein the ketone is dissolved in the acetic anhydride and treated with p-toluenesulfonic acid as catalyst, and the formed acetic acid is eliminated to obtain the corresponding enolacetate.

The encolacetates thus prepared are then converted into the enol-esters of formula (I) proceeding as follow.

A 500 ml three-neck flask under argon was charged with 0.05 mole of enolacetate and 75 ml of absolute tetrahydrofuran. The mixture was cooled to –60°/–70° (dry ice/acetone bath) and a solution of 6.16 g (0.055 mole) of t-BuOK in 60 ml of absolute THF was introduced dropwise (slightly exothermic, the reaction mixture becomes strongly yellow). Stirring was kept fair 1 h at –70° and 0.055 mole of the appropriate acyl chloride, in solution in 25 ml of absolute THF, were added dropwise. After 2 h at –70°, the cooling bath was removed and 60 ml of a saturated solution of $NaHCO_3$ were quickly added (the temperature rises quickly to –10°). The mixture was extracted twice with sulfuric ether, washed once with saturated $NaHCO_3$, once with water saturated with salt, dried ($Na_2SO_4$) and concentrated under vaccum. The product is then purified by flash-chromatography (column diameter=9 cm, hexane/ether 98:2) and, after combining the useful layers, concentrated to dry under absolute vaccum.

According to this method, there were prepared the following enol-esters:

a. 2-(4-tert-butylbenzyl)-1-propenyl acetate
Isomer (Z)
NMR($^1$H, 360 MHz, $CDCl_3$): 1.32(s, 9H); 1.59(s, 3H); 2.16(s, 3H); 3.43(s, 2H); 6.99(broad s, 1H); 7.10(d, J=8, 2H); 7.31(d, J=8, 2H) δ ppm.
NMR($^{13}$C, 90 MHz, $CDCl_3$): 17.4(q); 20.8(q); 31.4(q); 31.4(q); 31.4(q); 35.3(t); 125.3(d); 125.3(d); 128.3(d); 128.3 (d); 130.5(d); 34.4(s); 121.2(s); 136.0(s); 149.0(s); 168.3(s) δ ppm.

MS: 246(13, M$^+$); m/e, 204(17), 189(73), 171(7), 159(8), 147(31), 129(33), 119(100), 105(9), 91(40), 77(8), 71(7), 57(60), 43(64).
Isomer (E)
NMR($^1$H, 360 MHz, $CDCl_3$): 1.32(s, 9H); 1.62(s, 3H); 2.15(s, 3H); 3.24(s, 2H); 7.05(broad s, 1H); 7.12(d, J=8, 2H); 7.31(d, J=8, 2H) δ ppm.
NMR($^{13}$C, 90 MHz, $CDCl_3$): 13.6(q); 20.8(q); 31.4(q); 31.4(q); 31.4(q); 39.8(t); 125.3(d); 125.3(d); 128.4(d); 128.4 (d); 131.2(d); 34.4(s); 121.4(s); 135.9(s); 149.2(s); 168.3(s) δ ppm.
MS: 246(12, M$^+$); m/e, 204(41), 189(100), 171(3), 159 (7), 147(42), 131(21), 119(57), 105(9), 91(32), 77(6), 71(8), 57(45), 43(58).

b. 3,7-dimethyl-1,6-octadienyl acetate
The analytical characteristics of this compound were identical to those published in literature (see, D. P. Simmons et al., ref cited).

c. 3,7-dimethyl-1,6-octadienyl octanoate Isomer (Z)
NMR($^1$H, 360 MHz, $CDCl_3$): 0.89(t, J=7, 3H); 0.99(d, J=7, 3H); 1.30(m, 10H); 1.59(s, 3H); 1.68(s, 3H); 1.94(m, 2H); 2.39(t, J=7, 2H); 2.68(m, 1H); 4.67(dd, J$_1$=6, J$_2$=10, 1H); 5.10(m, 1H); 7.00(d, J=6, 1H) δ ppm.
NMR($^{13}$C, 90 MHz, $CDCl_3$): 14.1(q); 17.6(q); 20.9(q); 25.7(q); 22.6(t); 24.8(t); 25.9(t); 28.9(t); 29.0(t); 31.7(t); 34.2(t); 37.4(t); 29.4(d); 120.1(d); 124.5(d); 133.1(d); 131.3 (s); 171.0(s) δ ppm.
MS: 280(0, M$^+$); m/e, 198(1), 182(2), 154(8), 136(35), 127(100), 121(30), 109(20), 93(12), 82(17), 69(23), 57(96), 41(32).

Isomer (E)
NMR($^1$H, 360 MHz, $CDCl_3$): 0.89(t, J=7, 3H); 1.02(d, J=7, 3H); 1.30(m, 10H); 1.59(s, 3H); 1.68(s, 3H); 1.96(m, 1H); 2.15(m, 1H); 2.36(t, J=7, 2H); 5.07(m, 2H); 5.29(dd, J$_1$=8, J$_2$=12, 1H), 7.08(d, J=12, 1H) δ ppm.
NMR($^{13}$C, 90 MHz, $CDCl_3$): 14.1(q); 17.7(q); 20.9(q); 25.7(q); 22.6(t); 24.7(t); 25.7(t); 28.9(t); 29.1(t); 31.6(t); 34.1(t); 37.2(t); 32.0(d); 120.4(d); 124.3(d); 134.6(d); 131.5 (s); 171.2(s) δ ppm.
MS: 280(0, M$^+$); m/e, 198(1), 185(1), 154(7), 136(32), 127(93), 121(26), 109(19), 93(11), 82(15), 69(23), 57(100), 41(32).

d. 2-methyl-1-undecenyl acetate
Isomer (Z)
NMR($^1$H, 360 MHz, $CDCl_3$): 0.88(t, J=7, 3H); 1.27(m, 12H); 1.39(m, 2H; 1.63(split s, 3H); 2.11(m, 2H); 2.13(s, 3H); 6.83(broad s, 1H) δ ppm.
NMR($^{13}$C, 90 MHz, $CDCl_3$): 14.1(q); 17.4(q); 20.7(q); 22.7(t); 27.0(t); 29.3–29.6(t); 29.3–29.6(t); 29.3–29.6(t); 29.3–29.6(t); 29.3–29.6(t); 31.9(t); 120.0(d); 122.3(s); 168.3 (s) δ ppm.
MS: 226(3, M$^+$); m/e, 184(33), 166(1), 141(2), 124(3), 110(6), 95(14), 82(15), 71(100), 57(13), 43(50).
Isomer (E)
NMR($^1$H, 360 MHz, $CDCl_3$): 0.88(t, J=7, 3H); 1.27(m, 12H); 1.40(m, 2H); 1.66(split s, 3H); 1.95(m, 2H); 2.13(s, 3H); 6.88(broad s, 1H) δ ppm.
NMR($^{13}$C, 90 MHz, $CDCl_3$): 13.6(q); 14.1(q); 20.8(q); 22.7(t); 27.6(t); 29.2); 29.3(t); 29.5(t); 29.6(t); 31.9(t); 33.9 (t); 130.2(d); 122.0(s); 168.3(s) δ ppm.
MS: 226(2, M$^+$); m/e, 184(25), 166(1), 141(2), 123(3), 110(5), 95(12), 81(18), 71(100), 58(9), 43(40).

e. 2-methyl-1-undecenyl octanoate
Isomer (Z)
NMR($^1$H, 360 MHz, $CDCl_3$): 0.88(t, J=7, 6H); 1.27(m, 22H); 1.39(m, 2H); 1.52(split s, 3H); 2.10(t, J=7, 2H); 2.37(t, J=7, 2H); 6.85(broad s, 1H) δ ppm.
NMR($^{13}$C, 90 MHz, $CDCl_3$): 14 0(q); 14.1(q); 17.4(q); 22.6(t); 22.7(t); 24.9(t); 27.1(t); 28.9–29.6(t); 28.9–29.6(t);

28.9–29.6(t); 28.9–29.6(t); 28.9–29.6(t); 28.9–29.6(t); 28.9–29.6(t); 31.7(t); 31.9(t); 34.2(t); 129.9(d); 122.2(s); 171.1(s) δ ppm.

MS: 310(0, M⁺); m/e, 184(10), 127(85), 109(10), 95(6), 81(10), 71(25), 57(100), 43(10)

Isomer (E)

NMR(¹H, 360 MHz, CDCl₃): 0.88(t, J=7.6H; 1.27(m, 22H; 1.40(m, 2H; 1.67(split s, 3H; 1.95(t, J=7.2H); 2.39(t, J=7, 2H; 6.89(broad s, 1H) δ ppm.

NMR(¹³C, 90 MHz, CDCl₃): 13.6(q); 14.0(q); 14.1(q); 22.6(t); 22.7(t); 24.9(t); 27.6(t); 28.9–29.6(t); 28.9–29.6(t); 28.9–29.6(t); 28.9–29.6(t); 28.9–29.6(t); 28.9–29.6(t); 31.7(t); 31.9(t); 34.0(t); 34.2(t); 130.1(d); 121.9(s); 171.1(s) δ ppm.

MS: 310(0, M⁺); m/e, 184(10), 127(8), 109(10), 97(7), 81(13), 71(28), 57(100), 43(9)

f. 1-undecenyl acetate

Isomer (Z)

NMR(¹H, 360 MHz, CDCl₃): 0.88(t, J=7, 3H; 1.28(m, 12H; 1.37(m, 2H; 2.12(m, 2H; 2.14(s, 3H); 4.87(dt, J₁=J₂=6, 1H); 6.99(d, J=6, 1H) δ ppm.

NMR(hu 13C, 90 MHz, CDCl₃): 14.1(q); 20.8(q); 22.7(t); 24.4(t); 29.2–29.6(t); 29.2–29.6(t); 29.2–29.6(t); 29.2–29.6 (t); 29.2–29.6(t); 31.9(t); 114.4(d); 134.0(d); 168.2(s) δ ppm.

MS: 212(0, M⁺); m/e, 170(1), 152(3), 124(5), 110(6), 96(26), 82(34), 68(18), 57(33), 43(100).

Isomer (E)

NMR(¹H, 360 MHz, CDCl₃): 0.88(t, J=7, 3H); 1.27(m, 12H; 1.37(m, 2H); 1.99(q, J=7, 2H); 2.11(s, 3H); 5.41(dt, J₁=7, J₂=12, 1H); 7.06(d, J=12, 1H) δ ppm.

NMR(¹³C, 90 MHz, CDCl₃): 14.1(q); 20.7(q); 22.7(t); 27.3(t); 29.1–29.6(t); 29.1–29.6(t); 29.1–29.6(t); 29.1–29.6 (t); 29.1–29.6(t); 31.9(t); 115.1(d); 135.4(d), 168.3(s) δ ppm.

MS: 212(0, M⁺); m/e, 170(1), 152(4), 124(7), 110(8), 96(34), 82(41), 68(19), 57(39), 43(100).

g. 3-methyl-5-phenyl-1-pentenyl acetate

Isomer (Z)

NMR(¹H, 360 MHz, CDCl₃): 1.02(d, J=7, 3H); 1.54(m, 1H); 1.69(m, 1H); 2.10(s, 3H); 2.48–2.78(m, 3H); 4.72(dd, J₁=6, J₂=10, 1H); 7.03(d, J=6, 1H); 7.17(m, 3H); 7.26(m, 2H) δ ppm.

NMR(¹³C, 90 MHz, CDCl₃): 20.7(q); 21.0(q); 33.7(t); 38.9(t); 29.2(d); 119.8(d); 125.6(d); 128.2(d); 128.2(d); 128.4(d); 128.4(d); 133.4(d); 142.5(s); 168.1(s) δ ppm.

MS: 218(1, M⁺); m/e, 176(3), 158(3), 143(27), 131(10), 117(6), 104(16), 91(45), 71(43), 65(13), 51(7), 43(100).

Isomer (E)

NMR(¹H, 360 MHz, CDCl₃): 1.06(d, J=7, 3H); 1.62(m, 2H); 2.12(s, 3H); 2.18(m, 1H); 2.60(m, 2H); 5.33(dd, J₁=9, J₂=13, 1H); 7.09(d, J=13, 1H); 7.17(m, 3H); 7.27(m, 2H) δ ppm.

NMR(¹³C, 90 MHz, CDCl₃): 20.7(q); 21.0(q); 33.5(t); 38.8(t); 32.1(d); 120.3(d); 125.7(d); 128.3(d); 128.3(d); 128.4(d); 128.4(d); 134.9(d); 142.3(s); 168.3(s) δ ppm.

MS: 218(1, M⁺); m/e, 176(4), 158(34), 143(25), 131(9), 117(5), 104(16), 91(44), 71(48), 65(12), 51(6), 43(100).

h. 3-methyl-5-phenyl-1-pentenyl octanoate

Isomer (Z)

NMR(¹H, 360 MHz, CDCl₃): 0.89(t, J=7, 3H); 1.02(d, J=7, 3H); 1.30(m, 8H); 1.49–1.76(m, 4H); 2.36(t, J=7, 2H); 2.48–2.78(m, 3H); 4.72(dd, J₁=7, J₂=10, 1H); 7.05(d, J=7, 1H); 7.17(m, 3H); 7.26(m, 2H) δ ppm.

NMR(¹³C, 90 MHz, CDCl₃): 14.1(q); 21.0(q); 22.6(t); 24.7(t); 28.9(t); 29.0(t); 31.7(t); 33.7(t); 34.1(t); 38.9(t); 29.3(d); 119.7(d); 125.6(d); 128.2(d); 128.2(d); 128.4(d); 128.4(d); 133.4(d); 142.5(s); 171.0(s) δ ppm.

MS: 308(0, M⁺); m/e, 176(8), 158(78), 143(18), 127 (100), 104(36), 91(51), 71(10), 57(71), 43(14).

Isomer (E)

NMR(¹H, 360 MHz, CDCl₃): 0.89(t, J=7, 3H); 1.07(d, J=7,3H); 1.30(m, 8H); 1 65(m, 4H); 2.18(m, 1H); 2.37(t, J=7, 2H); 2.60(m, 2H); 5.33(dd, J₁=8, J₂=12,1H); 7.10(d, J=12,1H); 7.17(m, 3H); 7.27(m, 2H) δ ppm.

NMR(¹³C, 90 MHz, CDCl₃): 14.1(q); 21.0(q); 22.6(t); 24.7(t); 23.9(t); 29.0(t); 31.6(t); 33.6(t); 34.1(t); 38.9(t); 32.1(d); 120.1(d); 125.7(d); 128.3(d); 128.3(d); 128.4(d); 128.4(d); 135.0(d); 142.54(s); 171.1(s) δ ppm.

MS: 308(0, M⁺); m/e, 198(1), 176(10), 158(66), 143(20), 127(95), 104(34), 91(56), 71(13), 57(100), 43(20)

i. methyl 3-acetoxy-2-pentyl-2-cyclopentene-1-acetate

NMR(¹H, 360 MHz, CDCl₃): 0.88(t, J=7,3H); 1.28m, 5H); 1.41(m, 1H); 1.61(m, 1H); 1.79(m, 1H); 2.14(s, 3H); 2.03–2.26(m, 3H); 2.46(m, 2H); 2.56(dd, J₁=4, J₂=15, 1H; 3.04(m, 1H); 3.68(s, 3H) δ ppm.

NMR(¹³C, 90 MHz, CDCl₃): 14.0(q); 20.7(q); 51.5(q); 22.4(t); 24.4(t); 26.8(t); 27.2(t); 29.6(t); 31.7(t); 38.6(t); 39.7(d); 128.3(s); 145.4(s); 168.5(s); 173.2(s) δ ppm.

MS: 268(1, M⁺); m/e, 226(10), 208(2), 195(3), 169(3), 153(100), 137(4), 123(3), 109(10), 97(35), 83(10), 67(9), 55(8), 43(31).

j. methyl 3-octanoyloxy-2-pentyl-1-cyclopentene-1-acetate

NMR(¹H, 360 MHz, CDCl₃): 0.88(t, J=7, 3H); 0.89(t, J=7, 3H); 1.30(m, 14H); 1.53–1.72(m, 3H); 1.79(m, 1H); 2.08(m, 1H); 2.19(m, 2H); 2.31–2.51(m, 4H); 2.57(dd, J₁=4, J₂15, 1H); 3.05(m, ¹H); 3.68(s, 3H) δ ppm.

NMR(¹³C, 90 MHz, CDCl₃): 14.0(q); 14.1(q); 51.5(q); 22.4(t); 22.6(t); 24.5(t); 25.0(t); 26.8(t); 27.1(t); 28.9(t); 28.9(t); 29.6(t); 31.7(t); 31.7(t); 34.2(t); 38.6(t); 39.6(d); 128.2(s); 145.3(s); 171.5(s); 173.3(s) δ ppm.

MS: 352(0, M⁺); m/e, 279(2), 226(92), 208(3), 194(4), 169(4), 153(100), 127(12), 109(7), 97(6), 81(5), 67(5), 57(22), 43(10).

Example 4

Test on Fabrics

Several tests were carried out on fabrics, under a variety of conditions, said fabrics having been treated according to the following general method.

General Method of Treatment of Textiles

A standard cotton swatch of 32 g was placed in a Linitest® (origin: Hanau, Germany) type vessel containing 1.3 g of a standard powder detergent base comprising 1% by weight of lipase (Lipolase® 100T; origin: Novo Nordisk, Denmark) and 260 ml water. The cotton swatch was washed for 30 min at 40°. It was then taken out of the vessel and rinsed with 3×200 ml of water. It was then plunged for 5 min in 200 ml of water containing 0.6 g of a fabric softener base which contained a certain percentage by weight, comprised between 0.05 and 1%, of compound (I) according to the invention or, when applicable, of the corresponding alcohol, aldehyde or ketone. The cotton swatch was then spin-dried without having been used, and dried on a clothes line.

This method is equivalent to a washing in a real machine for washing 5 kg of linen in approximately 20 l of water, with a rinsing of 4×20 l water, the fabric softener being applied in the last rinsing water. The fabric softener base used had the following composition:

| Ingredients | % by weigth |
| --- | --- |
| Arquad 2 HT[1] (75%) | 5.00 |
| Formalin (40%) | 0.20 |

-continued

| Ingredients | % by weigth |
|---|---|
| Demineralized water | 94.69 |
| Colouring agent[2] | 0.11 |
| Total | 100.00 |

[1] origin: Akzo, Holland
[2] Colanyl Blau AR/10% sol.; origin: Hoechst, Germany In two separate tests, the cotton swatches were treated according to this general method, using as additive to the fabric softener respectively 9–decenyl hexadecanoate (1% by weighty in test A and 9-decenol (1% by weight) in test B.

The two swatches were submitted for a blind test evaluation 24 h after having been taken out of the Linitest® apparatus. The evaluation panel consisted of eight people, to whom had been given beforehand a smelling strip which had been dipped in 9-decen-1-ol, so as to render them familiar with the odour of this compound. The panel was then asked to smell the two cotton swatches above-mentioned and to indicate if they could identify the odour of 9-decen-1-ol in either of the swatches. Five amongst the eight members of the panel recognized the odour of this alcohol in the swatch treated in test A and indicated that this odour was very powerful, whereas only one of said members was able to identify the odour on the swatch treated in test B.

A further evaluation of the two swatches carried out by the same panel, under identical conditions, 24 h later, i.e. 48 h after talking the swatches out of the Linitest® apparatus, showed that none of the panel members could identify the odour of 9-decen-1-ol on the swatch of test B, whereas six of said members identified it without any hesitation on the swatch coming out of test A.

Similar results were obtained when the two compounds above-mentioned were present in the fabric softener at a rate of 0.5% by weight.

Example 5

Test on Fabrics

Nine standard cotton swatches (32 g each), numbered from 1 to 9, were separately treated, and in identical manners as described in Example 4, the only changing element being the additive incorporated in the fabric softener (at 1% by weight) and described in Table 1 hereinafter.

TABLE 1

| COTTON SWATCH | SOFTENER ADDITIVE |
|---|---|
| 1 | 9-decen-1-ol |
| 2 | 9-decenyl octanoate |
| 3 | 9-decenyl nonanoate |
| 4 | 9-decenyl decanoate |
| 5 | 9-decenyl undecanoate |
| 6 | 9-decenyl dodecanoate |
| 7 | 9-decenyl tridecanoate |
| 8 | 9-decenyl tetradecanoate |
| 9 | 9-decenyl pentadecanoate |

24 H after taking the swatches out of the Linitest® machines, the nine cotton scratches were submitted for a blind evaluation to a panel consisting of ten individuals, whom, after having smelled 9-decen-1-ol on a smelling strip, had to indicate whether they recognized me odour of this alcohol on any one of the swatches. The result of this evaluation is summarized on Table 2 hereafter (only categorical identifications were taken into account):

TABLE 2

| COTTON SWATCH | Number of panel members having recognized the odour |
|---|---|
| 1 | 0 |
| 2 | 10 |
| 3 | 8 |
| 4 | 3 |
| 5 | 6 |
| 6 | 10 |
| 7 | 8 |
| 8 | 7 |
| 9 | 9 |

In a similar test carried out 48 h after having taken the swatches out of the Linitest® machine, the members of the panel were still unanimous as regards swatch 1, i.e. they could not recognize the odour of 9-decen-1-ol on this swatch, whereas a majority judged it still very powerful on all the other swatches.

Example 6

Test on Fabrics

Six standard cotton swatches (32 g each), numbered from 1 to 6, were separately treated, and in identical manner, as described in Example 4, the only changing element being the additive incorporated in the fabric softener, at 1% by weight) and described in Table 3 hereinafter.

TABLE 3

| COTTON SWATCH | SOFTENER ADDITIVE |
|---|---|
| 1 | 9-decen-1-ol |
| 2 | bis(9-decenyl) oxalate |
| 3 | bis(9-decenyl) malonate |
| 4 | bis(9-decenyl) butanedioate |
| 5 | bis(9-decenyl) pentanedioate |
| 6 | bis(9-decenyl) hexanedioate |

24 H after taking the swatches out of the Linitest® machines, the six cotton swatches were submitted for a blind evaluation to a panel consisting of ten individuals, whom, after having smelled 9-decen-1-ol on a smelling strip, had to indicate whether they recognized the odour of this alcohol on any one of the swatches. The result of this evaluation is summarized on Table 4 hereafter (only categorical identifications were taken into account):

TABLE 4

| COTTON SWATCH | Number of panel members having recognized the odour after 24 h |
|---|---|
| 1 | 0 |
| 2 | 10 |
| 3 | 6 |
| 4 | 8 |
| 5 | 9 |
| 6 | 7 |

The same test, carried out 48 h after having taken the swatches out of die Linitest® machines, gave the results summarized in Table 5 hereinafter:

TABLE 5

| COTTON SWATCH | Number of panel members having recognized the odour after 48 h |
| --- | --- |
| 1 | 0 |
| 2 | 10 |
| 3 | 7 |
| 4 | 6 |
| 5 | 8 |
| 6 | 7 |

Example 7

Test on Fabric

Six standard cotton swatches (32 g each), numbered from 1 to 6, were separately treated, and in identical manner, as described in Example 4. The detergent's content in lipase was now 3% by weight and the amount of fabric softener added to the last rinsing water was now 1.2 g. the additive incorporated (at 1% by weight) into the fabric softener in each case is cited in the following Table 6:

TABLE 6

| COTTON SWATCH | SOFTENER ADDITIVE |
| --- | --- |
| 1 | (E)-3,7-dimethyl-2,6-octadien-1-ol |
| 2 | (E,E)-bis(3,7-dimethyl-2,6-octadienyl) oxalate |
| 3 | (E,E)-bis(3,7-dimethyl-2,6-octadienyl) malonate |
| 4 | (E,E)-bis(3,7-dimethyl-2,6-octadienyl) butanedioate |
| 5 | (E,E)-bis(3,7-dimethyl-2,6-octadienyl) pentanedioate |
| 6 | (E,E)-bis(3,7-dimethyl-2,6-octadienyl) hexanedioate |

24 H after taking the swatches out of the Linitest® machines, the six cotton swatches were submitted for a blind evaluation to a panel consisting of ten individuals, whom, after having smelled (E)-3,7-dimethyl-2,6-octadien-1-ol on a smelling strip, had to indicate whether they recognized the odour of this alcohol on any one of the swatches. The result of this evaluation is summarized on Table 7 hereafter (only categorical identifications were taken into account):

TABLE 7

| COTTON SWATCH | Number of panel members having recognized the odour |
| --- | --- |
| 1 | 2 |
| 2 | 7 |
| 3 | 7 |
| 4 | 9 |
| 5 | 7 |
| 6 | 8 |

Example 8

Test on Fabrics

Two standard cotton swatches (32 g each), numbered 1 and 2, were separately treated, and in identical manner, as described in Example 4, the only changing element being the additive incorporated in the fabric softener and described in Table 8 hereinafter.

TABLE 8

| COTTON SWATCH | SOFTENER ADDITIVE |
| --- | --- |
| 1 | 3,7-dimethyl-6-octen-1-ol |
| 2 | 3,7-dimethyl-6-octenyl hexadecanoate |

24 H after taking the swatches out of the Linitest® machines, the two cotton swatches were submitted for a blind evaluation to a panel consisting of eleven individuals, whom, after having smelled (E)-3,7-dimethyl-6-octen-1-ol on a smelling strip, had to indicate whether they recognized the odour of this alcohol on one or the other of the swatches. The result of this evaluation is summarized on Table 9 hereafter (only categorical identifications were taken into account):

TABLE 9

| COTTON SWATCH | Number of panel members having recognized the odour |
| --- | --- |
| 1 | 0 |
| 2 | 7 |

A similar test carried out with two cotton swatches treated with the same fabric softener base but containing only 0.5% by weight of the compounds reported in Table 8. The panel evaluation showed that none of the panel members was able to identify the odour of the alcohol on swatch 1, whereas 7, of the 11 members of the panel were certain that they could smell it on swatch 2.

Still analogous results were obtained with a dosage of 0.1% by weight of the above mentioned compounds.

Example 9

Test on Fabrics

Three standard cotton swatches (32 g each), numbered from 1 to 3, were separately treated, and in identical manner, as described in Example 4, the only changing element being the additive incorporated in the fabric softener (at 1% by weight) and described in Table 10 hereinafter.

TABLE 10

| COTTON SWATCH | SOFTENER ADDITIVE |
| --- | --- |
| 1 | 3-methyl-5-phenylpentan-1-ol |
| 2 | 3-methyl-5-phenylpentyl octanoate |
| 3 | 3-methyl-5-phenylpentyl hexadecanoate |

24 H after taking the swatches out of the Linitest® machines, the three cotton swatches were submitted for a blind evaluation to a panel consisting of ten individuals, whom, after having smelled 3-methyl-5-phenylpentan-1-ol on a smelling strip, had to indicate whether they recognized the odour of this alcohol on any one of the swatches. The result of this evaluation is summarized on Table 11 hereafter (only categorical identifications were taken into account):

TABLE 11

| COTTON SWATCH | Number of panel members having recognized the odour |
|---|---|
| 1 | 2 |
| 2 | 6 |
| 3 | 5 |

Example 10

Test on Fabrics

Three standard cotton swatches (32 g each) were treated separately following the general method described in Example 4, two of said swatches (1 et 2) using 9-decen-1-ol as additive to the softener, and swatch 3 using as additive 9-decenyl hexadecanoate, these additives having been added to the fabric softener in a concentration of 0.5% by weight.

The three swatches were evaluated on a blind test by a panel of 12 individuals 24 h after having been taken out of the Linitest® machines. The members of the panel were asked if they could ascertain any difference amongst the swatches and, if applicable, whether they could qualify this difference. The panel had previously smelled strips dipped in 9-decen-1-ol and was aware that an evaluation of the three cotton swatches with regard to the particular odour of this compound was expected.

As a result of this evaluation, 8 out of the 12 members of the panel chose swatch 3 as being the one olfactively distinct and indicated that it developed the characteristic odour of 9-decen-1-ol, whilst the other two swatches gave off no distinctive odour.

The same test was carried out with 1% of additive in the softener, instead of 0.5%. In this case, 9 of the 12 members of the panel chose once again swatch 3 as being the one developing the odour of the above-mentioned alcohol, and indicated that this odour was even more powerful than in the preceding test. On the other hand, the panel found that the other two cotton swatches still exhaled no distinctive odour.

Example 11

Test on Fabrics

Two standard cotton swatches (32 g each), numbered 1 and 2, were separately treated, and in identical manner, as described in Example 4, the only changing element being the additive incorporated in the fabric softener at a rate of 0.05% by weight, and described in Table 12 hereinafter.

TABLE 12

| COTTON SWATCH | SOFTENER ADDITIVE |
|---|---|
| 1 | 3,7-dimethyl-2,6-octadien-1-ol |
| 2 | 3,7-dimethyl-2,6-octadienyl hexadecanoate |

24 H after talking the swatches out of the Linitest® machines, the two cotton swatches were submitted for a blind evaluation to a panel consisting of twelve individuals, whom, after having smelled 3,7-dimethyl-2,6-octadien-1-ol on a smelling strip, had to indicate whether they recognized the odour of this alcohol on one or the other of the swatches.

The result of this evaluation is summarized on Table 13 hereafter (only categorical identifications were taken into account):

TABLE 13

| COTTON SWATCH | Number of panel members having recognized the odour |
|---|---|
| 1 | 0 |
| 2 | 8 |

Example 12

Test on Fabrics

Two standard cotton swatches (32 g each), numbered 1 and 2, were separately treated, and in identical manner, as described in Example 4, but adding to the fabric softener 1% by weight of the additives cited in Table 14 hereinafter.

TABLE 14

| COTTON SWATCH | SOFTENER ADDITIVE |
|---|---|
| 1 | 3,7-dimethyl-6-octenal |
| 2 | 3,7-dimethyl-1,6-octadienyl octanoate |

24 H after taking the swatches out of the Linitest® machines, the two cotton swathes were submitted for a blind evaluation to a panel consisting of eleven individuals, whom, after having smelled 3,7-dimethyl-6-octenal on a smelling strip, had to indicate whether they recognized the odour of this aldehyde on one or the other of the swatches. The result of this evaluation is summarized on Table 15 hereafter (only categorical identifications were taken into account):

TABLE 15

| COTTON SWATCH | Number of panel members having recognized the odour |
|---|---|
| 1 | 4 |
| 2 | 11 |

Example 13

Test on Fabrics

Two standard cotton swatches (32 g each), numbered 1 and 2, were separately treated, and in identical manner, as described in Example 4, the only changing element being the additive incorporated (at 1% by weight) in the fabric softener and described in Table 16 hereinafter.

TABLE 16

| COTTON SWATCH | SOFTENER ADDITIVE |
|---|---|
| 1 | 3-methyl-5-phenyl-1-pentanal |
| 2 | 3-methyl-5-phenyl-1-pentenyl octanoate |

24 H after taking the swatches out of the Linitest® machines, the two cotton swatches were submitted for a blind evaluation to a panel consisting of twelve individuals, whom, after having smelled 3-methyl-5-phenyl-1-pentanal on a smelling strip, had to indicate whether they recognized the odour of this aldehyde on one or the other of the swatches. The result of this evaluation is summarized on Table 17 hereafter (only categorical identifications were taken into account):

TABLE 17

| COTTON SWATCH | Number of panel members having recognized the odour |
|---|---|
| 1 | 2 |
| 2 | 8 |

Example 14

Test on Fabrics

Three standard cotton swatches (32 g each) were treated separately following the general method described in Example 4, two of said swatches (1 et 2) using 2-methyl-1-undecanal as additive to the softener, and swatch 3 using as additive 2-methyl-1-undecenyl octanoate, these additives having been added to the fabric softener in a concentration of 0.1% by weight.

The three swatches were evaluated on a blind test by a panel of 12 individuals 24 h after having been taken out of the Linitest® machines. The members of the panel were asked if they could ascertain any difference amongst the swatches and, if applicable, whether they could qualify this difference. The panel had previously smelled strips dipped in 2-methyl-1-undecanal and was aware that an evaluation of the three cotton swatches with regard to the particular odour of this compound was expected.

As a result of this evaluation, 10 out of the 12 members of the panel chose swatch 3 as being the one olfactively distinct and indicated that it developed the characteristic odour of 2-methyl-1-undecanal, whereas the other two swatches gave off no distinctive odour.

Example 15

Test on Fabrics Treated in a Washing Machine

Two standard batches of cotton textiles, each comprising 30 cotton swatches (32 g each), were put into two separate washing machines, each containing, in the detergent compartment, 130 g of a standard powder detergent base comprising 1% by weight of lipase (Lipolase® 100T; origin: Novo Nordisk, Denmark). In the compartment intended for the fabric softener, there was put, in one of the cases, 100 g of a softener base such as described in Example 4, perfumed with 0.1% by weight of 2-methyl-1-undecanal, whereas the softener (100 g) put in the second machine contained 0.1% by weight of 2-methyl-1-undecenyl octanoate. The batches of swatches were then washed with a normal washing cycle, at 40°, without prewash, and air dried.

The batches of swatches were evaluated on a blind test, 24 h after having been taken out of the machines, by a panel of 36 individuals. The latter had to indicate if they found any difference at all amongst the three batches of swatches, of which two were identical and had been treated with the softener containing 2-methyl-1-undecanal (batches 1 and 2) and the third had been treated with 2-methyl-1-undecenyl octanoate (batch 3), without qualifying the nature of the distinctive character. In addition, they were also asked to indicate whether any one of the batches possessed a more powerful odious.

Of the 36 panellists, 24 identified textile batch 3 as being the one distinct from the other two, from an olfactive point of view, and indicated that this batch possessed a stronger odour than the other two.

An analogous test was carried out but with only two textile batches, batch A having been treated with a softener containing 0.05% by weight of 2-methyl-1-undecanal and batch B with a softener containing 0.05% by weight of the corresponding enol-ester, i.e. 2-methyl-1-undecenyl octanoate.

The panel of 36 individuals which evaluated batches A and B, without knowing the nature of the perfuming ingredients, had to indicate which of the two batches developed a stronger odour and which was preferred from the point of view of the perception of freshness and cleanliness of the linen.

According to the categoric opinion of 32 out of the 36 panellists, the textiles batch B was far more "perfumed" than batch A and was perceived as being cleaner, with a more fresh odour.

Example 16

Tests on Fabrics Treated in a Washing Machine

A base perfuming composition was prepared by admixing the following ingredients:

| Ingredients | % by weight |
|---|---|
| Benzyl acetate | 30 |
| 1,1-Dimethyl-2-phenylethyl acetate | 25 |
| 10-Undecenal | 3 |
| Hexylcinnamic aldehyde | 150 |
| Methyl anthranilate dist. | 10 |
| Cedroxyde ®[1] | 40 |
| 10%* Ambrox ®[2] DL | 2 |
| Verdyl acetate[3] | 30 |
| 10%* α-Damascone | 3 |
| Dihydromyrcenol[4] | 80 |
| 10%* Dynascone ®[5] | 2 |
| Eugenol | 7 |
| Exaltex ®[6] | 50 |
| Galbex ®[7] 183 | 8 |
| Geranyl nitrile | 1 |
| 10%** Indol | 5 |
| Iralia ®[8] | 20 |
| Isoeugenol | 3 |
| Lilial ®[9] | 50 |
| Linalol | 30 |
| Lorysia ®[10] | 50 |
| Mayol ®[11] | 10 |
| Hedione ®[12] | 50 |
| 10%* Rose oxide[13] | 5 |
| Phenethylol | 60 |
| Polysantol ®[14] | 3 |
| Orange essential oil | 40 |
| Benzyl salicylate | 30 |
| Scentenal ®[15] | 3 |
| Terpineol | 25 |
| Veloutone[16] | 2 |
| Verdox ®[17] | 20 |

| Ingredients | % by weight |
| --- | --- |
| β-Naphtol methyl-ether | 2 |
| Zestover ®[18] | 1 |
| Total | 850 |

*in dipropyleneglycol (DIPG)
**in triethanolamine

[1] trimethyl-13-oxabicyclo[10.1.0]trideca-4,8-diene; origin: Firmenich SA, Geneva, Switzerland
[2] dodecahydro-3,6,6,9a-tetramethyl-naphto[2,1-b]furan; origin: Firmenich SA, Geneva, Switzerland
[3] tricyclo[5.2.1.0$^{2,6}$]dec-3-en-8-yl acetate; origin: Givaudan-Roure, Vernier, Switzerland
[4] 2,6-dimethyl-7-octen-2-ol; origin: International Flavors & Fragrances, USA
[5] 1-(5,5-dimethyl-1-cyclohex-1-yl)-4-penten-1-one; origin: Firmenich SA, Geneva, Switzerland
[6] oxacyclohexadecan-2-one; origin: Firmenich SA, Geneva, Switzerland
[7] origine: Firmenich SA, Geneva, Switzerland
[8] methylionone; origin: Firmenich SA, Geneva, Switzerland
[9] 3-(4-tert-butyl-1-phenyl)-2-methylpropanal; origin: Givaudan-Roure, Vernier, Switzerland
[10] 4-(1,1-dimethylethyl)-cyclohexanol acetate; origin: Firmenich SA, Geneva, Switzerland
[11] cis-4-(1-methylethyl)-cyclohexanemethanol; origin: Firmenich SA, Geneva, Switzerland
[12] methyl ester of 3-oxo-1-pentyl-cyclopentaneacetic acid; origin: Firmenich SA, Geneva, Switzerland
[13] origin: Firmenich SA, Geneva, Switzerland
[14] 3,3-dimethyl-5-(2,2,3-trimethyl-3-cyclopenten-1-yl)-4-penten-2-ol; origin: Firmenich SA, Geneva, Switzerland
[15] octahydro-5-methoxy-4,7-methano-1H-indene-2-carboxaldehyde; origin: Firmenich SA, Geneva, Switzerland
[16] 2,2,5-trimethyl-5-pentyl-cyclopentanone; origin: Firmenich SA, Geneva, Switzerland
[17] 2-tert-butyl-cyclohexanyl acetate; origin: International Flavors & Fragrances, USA
[18] 2,4-dimethyl-3-cyclohexene-1-carbaldehyde; origin: Firmenich SA, Geneva, Switzerland Two perfuming compositions were prepared win this base composition, by adding thereto 150 parts by weight of geraniol or 3,7-dimethyl-2,6-octadienol (composition A), respectively 150 parts by weight of 3,7-dimethyl-2,6-octadienyl hexadecanoate (composition B).

These turf, perfuming compositions were then added, at the rate of 0.6% by weight, to a non-perfumed fabric softener base to prepare two samples, A and respectively B, of a perfumed softener.

In two identical washing machines, mere were treated two standard batches of textiles, each formed of 1400 g of varied linen, comprising cotton swatches, cotton textiles and textiles in a cotton/polyester mixture. Each machine was charged with 130 g of a standard unperfumed detergent base containing 1% of lipase (Lipolase® 100T). One of the machines was also charged with 100 g of sample A of the softener, comprising geraniol, whereas to the second machine there were added 100 g of softener sample B.

The linen was then washed at 40° in a normal washing cycle, without prewash, and dried to air for 24 h.

Three standard batches of textiles, of which two were identical and had been treated with sample A and the third with sample B, were then evaluated on a blind test by a panel of 20 individuals, who had to identify the batch of textiles possessing a distinct odour from that of the other two, without qualifying the nature of the distinctive character. The panellists also had to indicate which of the textile batches was more perfumed.

As a result of this test, 14 panellists perceived a distinction in the odour of the textile batch treated with the fabric softener sample 8, while 10 out of these 14 indicated that this same batch was the more perfumed.

When the evaluation was repeated after 48 h of drying to air, analogous results were obtained.

We claim:

1. A perfuming composition comprising, as an active ingredient, a compound formula

wherein a. R represents a monovalent radical derived from a fragrant alcohol of formula ROH and Y represents a $C_7$ to $C_{24}$ linear or branched, saturated or unsaturated hydrocarbon radical, or a —$(CH_2)_n$COOR group wherein R is defined as above and n is an integer from 0 to 6; or b. Y represents a $C_7$ to $C_{24}$ linear or branched, saturated or unsaturated hydrocarbon radical and R represents a group of formula

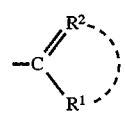

wherein, either $R^1$ represents hydrogen and $R^2$ represents an alkylidene radical derived from a fragrant aldehyde of formula

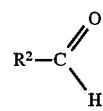

or $R^1$ and $R^2$ are derived from a fragrant ketone of formula

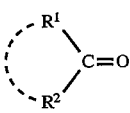

and, taken separately, represent respectively an alkyl radical and an alkylidene radical, or, taken together with their terminal C atoms, represent a substituted or unsubstituted cyclic alkyl, alkenyl, aryl or alkylaryl moiety having 5 to 18 carbon atoms as part of a ring which is indicated by the dotted line.

2. A composition according to claim 1, wherein said active perfuming ingredient is a compound of formula (I) in which Y represents a $C_7$ to $C_{24}$ linear or branched, saturated or unsaturated hydrocarbon radical.

3. A composition according to claim 1, wherein said active perfuming ingredient is a compound of formula (I) in which Y represents a $C_{12}$ to $C_{24}$ linear or branched, saturated or unsaturated hydrocarbon radical.

4. A composition according to claim 1, wherein said active perfuming ingredient is a compound of formula (I) in which R is a monovalent radical derived from a fragrant alcohol selected from the group consisting of anisic alcohol, cinnamic alcohol, fenchylic alcohol, 9-decen-1-ol, phenethylol, citronellol, 3-methyl-5-phenyl-1-pentanol, 7-p-menthan-1-ol, 2,6-dimethyl-7-octen-2-ol, 3,7-dimethyl-2,6-octadien-1-ol, 3-hexen-1-ol, 1-hexanol, 2-hexanol, 5-ethyl-2-nonanol, 2,6-nonadien-1-ol, borneol, 1-octen-3-ol, 4-cyclohexyl-2-methyl-2-butanol, 2-methyl-4-phenyl-2- butanol, 2-methyl-1-phenyl-2-propanol, cyclomethylcitronellol, decanol, dibydroeugenol, 8-p-menthanol, 3,7-dimethyl-1-octanol, 2,6-dimethyl-2-heptanol, dodecanol, eucalyptol, eugenol, tetrahydro-2-isobutyl-4-methyl-4(2H)pyranol, isoeugenol, linalol, 2-methoxy-4-propyl-1-cyclohexanol, terpineol, tetrahydromuguol, 3,7-dimethyl-3-octanol, 3-(4-hydroxy-4-methylpentyl)-cyclohex-3-ene-1-carbaldehyde and 4-(4-hydroxy-4-methylpentyl)-cyclohex-3-ene-1-carbaldehyde.

5. A composition according to claim 1, wherein said active perfuming ingredient is a compound of formula (I) in which R stands for a group of formula

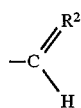

$R^2$ representing a radical derived from a fragrant aldehyde selected from the group consisting of the $C^6$ to $C^{12}$ aldehydes, hydrotropic aldehyde, methyl nonyl acetaldehyde, phenylpropanoic aldehyde, 3- or 4-(4-methyl-3-pentenyl)-3-cyclohexene-1-carbaldehyde, 2-methyldecanal, 4-isopropyl-1-benzeneacetaldehyde, (4-methyl-1-phenyl)acetaldehyde, 6-nonenal, citral, citronellal, 9-decenal, 3-(4-isopropyl-1-phenyl)-2-methylpropanal, 2,4-heptadienal, 2,4-nonadienal, 2,4-decadienal, 5,9-dimethyl-4,9-decadienal, 6-octenal, 2,6,10-trimethyl-9-undecenal, 3-(4-methoxy-1-phenyl)-2-methylpropanal, 3-(1,3-benzodioxol-5-yl)-2-methylpropanal, 4-heptenal, 3,5,5-trimethylhexanal, (4-methyl-1-phenoxy) acetaldehyde, hydroxycitronellal, isocyclocitral, 3-(4-tert-butyl-1-phenyl)-2-methylpropanal, 1-p-menthene-9-carbaldehyde, 3- or 4-(4-hydroxy-4-methylpentyl)-3-cyclohexene-1-carbaldehyde, 2,6-dimethyl-5-heptenal, 1-p-menthen-9-al, 2-octenal, 2,6-nonadienal, 3-methyl-5-phenylpentanal, 4-decenal, 2-undecenal, 3,7-dimethyloctanal, 2,4-dimethyl-3-cyclohexene 1-carbaldehyde, 3-phenylbutanal, octahydro-5-methoxy-4,7-methano-1H-indene-2-carboxaldehyde, 2,5,9-trimethyl-4,9-decadienal, undecenal, 4-methyl-phenyl-propanoic aldehyde and 3-(4-tertbutyl-1-phenyl) propanal.

6. A composition according to claim 1, wherein said active perfuming ingredient is a compound of formula (I) in which R stands for a group of formula

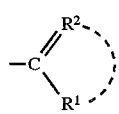

$R^1$ and $R^2$ representing radicals derived from a fragrant ketone selected from the group consisting of 4-(4-hydroxy-1-phenyl)-2-butanone, benzylacetone, an ionone, carvone, 3,7-dimethyl-1,1-bis(11-methyldodecyloxy)-2,6-octadiene, muscone, 2-pentyl-1-cyclopentanone, ethyl amyl ketone, ethyl pentyl ketone, 2-heptyl-1-cyclopentanone, genarylketone, methylionone, 1-(octahydro-2,3,8,8-tetramethyl-2-naphtalenyl)-1-ethanone, 6-methyl-5-hepten-2-one, methyl jasmonate, methyl hexyl ketone, methyl pentyl ketone, methyl nonyl ketone, cis-jasmone, methyl dihydrojasmonate, civettone, 4-(1,1-dimethylpropyl)-1-cyclohexanone, cyclopenta-decanone, 2,6,6-trimethyl-2-cyclohexene-1,4-dione, p-tert-butylcyclohexanone, tricyclo [6.2.1.0$^{2,7}$]undec-9-en-3-one, 10,10-dimethyl-tricyclo [7.1.1.0$^{2,7}$]undec-2-en-4-one, perhydro-5,5,8a-trimethyl-2-naphtalenone and 5-methyl-exo-tricyclo[6.2.1.0$^{2,7}$]undecan-4-one.

7. A composition according to claim 1, wherein said active perfuming ingredient is a compound of formula (I) wherein R is the radical 9-decen-1-yl,-3,7-dimethyl-2,6-octadien-1-yl, 3,7-dimethyl-6-octen-1-yl, 3-methyl-5-phenylpentyl, 3,7-dimethyl-1,6-octadienyl, 3-methyl-5-phenyl-1-pentenyl or 2-methyl-1-undecenyl.

8. A composition according to claim 2, wherein said active perfuming ingredient is a compound of formula (I) wherein R is the radical 9-decen-1-yl,-3,7-dimethyl-2,6-octadien-1-yl, 3,7-dimethyl-6-octen-1-yl, 3-methyl-5-phenylpentyl, 3,7-dimethyl-1,6-octadienyl, 3-methyl-5-phenyl-1-pentenyl or 2-methyl-1-undecenyl.

9. A composition according to claim 3, wherein said active perfuming ingredient is a compound of formula (I) wherein R is the radical 9-decen-1-yl,-3,7-dimethyl-2,6-octadien-1-yl, 3,7-dimethyl-6-octen-1-yl, 3-methyl-5-phenylpentyl, 3,7-dimethyl-1,6-octadienyl, 3-methyl-5-phenyl-1-pentenyl or 2-methyl-1-undecenyl.

10. A laundry detergent or fabric softener comprising, as active perfuming ingredient, a compound of formula

wherein a. R represents a monovalent radical derived from a fragrant alcohol of formula ROH and Y represents a $C_7$ to $C_{24}$ linear or branched, saturated or unsaturated hydrocarbon radical, or a —$(CH_2)_n$COOR Group wherein R is defined as above and n is an integer from 0 to 6; or b. Y represents a $C_7$ to $C_{24}$ linear or branched, saturated or unsaturated hydrocarbon radical and R represents a group of formula

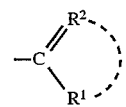

wherein, either $R^1$ represents hydrogen and $R^2$ represents an alkylidene radical derived from a fragrant aldehyde of formula

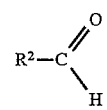

or $R^1$ and $R^2$ are derived from a fragrant ketone of formula

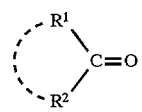

and, taken separately, represent respectively an alkyl radical and an alkylidene radical, or, taken totether with their terminal C atoms, represent a substituted or unsubstituted cyclic alkyl, alkenyl, aryl or alkylaryl moiety having 5 to 18 carbon atoms as part of a ring which is indicated be the dotted line.

11. A laundry detergent or fabric softener according to claim 10, wherein said compound of formula (I) is selected from the group consisting of 2-phenylethyl octanoate, 2-phenylethyl hexadecanoate, 3,7-dimethyl-6-octenyl octanoate, 3,7-dimethyl-6-octenyl hexadecanoate, 3-methyl-5-phenyl-1-pentyl octanoate, 3-methyl-5-phenyl-1-pentyl hexadecanoate, 7-p-menthanyl octanoate, 9-decenyl octanoate, 9-decenyl-nonanoate, 9-decenyl decanoate, 9-decenyl undecanoate, 9-decenyl dodecanoate, 9-decenyl tridecanoate, 9-decenyl tetradecanoate, 9-decenyl pentadecanoate, 9-decenyl hexadecanoate, 1-methylpentyl hexadecanoate, 7-p-methanyl hexadecanoate, hexyl hexadecanoate, (Z)-3-hexenyl hexadecanoate, (E)-3,7-dimethyl-2,6-octadienyl hexadecanoate, bis(9-decenyl) oxalate, bis(9-decenyl) malonate, bis(9-decenyl) butanedioate, bis(9-decenyl) pentanedioate, bis(9-decenyl) hexanedioate, (E,E)-bis(3,7-dimethyl-2,6-octadienyl) oxalate, (E,E)-bis(3,7-dimethyl-2,6-octadienyl) malonate, (E,E)-bis(3,7-dimethyl-2,6-octadienyl) butanedioate, (E,E)-bis(3,7-dimethyl-2,6-octadienyl) pentanedioate, (E,E)-bis(3,7-dimethyl-2,6-octadienyl)hexanedioate, 2-(4-tert-butylbenzyl)-1-propenyl acetate, 3,7-dimethyl-1,6-octadienyl acetate, 3,7-dimethyl-1,6-octadienyl octanoate, 2-methyl-1-undecenyl acetate, 2-methyl-1-undecenyl octanoate, 1-undecenyl acetate, 3-methyl-5-phenyl-1-pentenyl acetate, 3-methyl-5-phenyl-1-pentenyl octanoate, methyl-3-acetoxy-2-pentyl-2-cyclopentene-1-acetate and methyl-3-octanoyloxy-2-pentyl-1-cyclopentene-1-acetate.

12. A laundry detergent or fabric softener comprising a perfuming composition comprising, as an active perfuming ingredient, a compound of formula

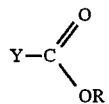

(I)

wherein a. R represents a monovalent radical derived from a fragrant alcohol of formula ROH and Y represents a $C_7$ to $C_{24}$ linear or branched, saturated or unsaturated hydrocarbon radical, or a —$(CH_2)_n COOR$ group wherein R is defined as above and n is an integer from 0 to 6; or b. Y represents a $C_7$ to $C_{24}$ linear or branched, saturated or unsaturated hydrocarbon radical and R represents a group of formula

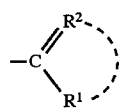

wherein, either $R^1$ represents hydrogen and $R^2$ represents an alkylidene radical derived from a fragrant aldehyde of formula

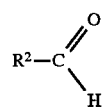

or $R^1$ and $R^2$ are derived from a fragrant ketone of formula

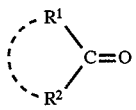

and, taken separately, represent respectively an alkyl radical and an alkylidene radical, or, taken together with their terminal C atoms, represent a substituted or unsubstituted cyclic alkyl, alkenyl, aryl or alkylaryl moiety having 5 to 18 carbon atoms as part of a ring which is indicated by the dotted line.

13. A method for perfuming fabrics, which comprises washing said fabrics in the presence of a lipase-containing detergent, and, optionally, subsequently treating said fabrics with a fabric softener, wherein said detergent and/or said fabric softener comprises, as active perfuming ingredient, a compound of formula

wherein a. R represents a monovalent radical derived from a fragrant alcohol of formula ROH and Y represents a $C_7$ to $C_{24}$ linear or branched, saturated or unsaturated hydrocarbon radical, or a —$(CH_2)_n COOR$ group wherein R is defined as above and n is an integer from 0 to 6; or b. Y represents a $C_7$ to $C_2 4$ linear or branched, saturated or unsaturated hydrocarbon radical and R represents a group of formula

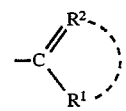

wherein, either $R^1$ represents hydrogen and $R^2$ represents an alkylidene radical derived from a fragrant aldehyde of formula

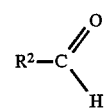

or $R^1$ and $R^2$ are derived from a fragrant ketone of formula

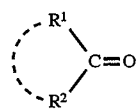

and, taken separately, represent respectively an alkyl radical and an alkylidene radical, or, taken together with their terminal C atoms, represent a substituted or unsubstituted cyclic alkyl, alkenyl, aryl or alkylaryl moiety having 5 to 18 carbon atoms as part of a ring which is indicated by the dotted line.

14. A method according to claim 13, wherein said fabrics, after the washing cycle, are treated with a fabric softener containing a compound of formula (I).

15. A method according to claim 13, wherein said detergent or said fabric softener contains a compound of formula (I) in which R is a monovalent radical derived from a fragrant alcohol selected from the group consisting of anisic alcohol, cinnamic alcohol, fenchylic alcohol, 9-decen-1-ol, phenethylol, citronellol, 3-methyl-5-phenyl-1-pentanol, 7-p-menthan-1-ol, 2,6-dimethyl-7-octen-2-ol, 3,7-dimethyl-2,6-octadien-1-ol, 3-hexen-1-ol, 1-hexanol, 2-hexanol, 5-ethyl-2-nonanol, 2,6-nonadien-1-ol, borneol, 1-octen-3-ol, 4-cyclohexyl-2-methyl-2-butanol, 2-methyl-4-phenyl-2-butanol, 2-methyl-1-phenyl-2-propanol, cyclomethylcitronellol, decanol, dihydroeugenol, 8-p-menthanol, 3,7-dimethyl-1-octanol, 2,6-dimethyl-2-heptanol, dodecanol, eucalyptol, eugenol, tetrahydro-2-isobutyl-4-methyl-4(2H)pyranol, isoeugenol, linalol, 2-methoxy-4-propyl-1-cyclohexanol, terpineol, tetrahydromuguol, 3,7-dimethyl-3-octanol, 3-(4-hydroxy-4-methylpentyl)-cyclohex-3-ene-1-carbaldehyde and 4-(4-hydroxy-4-methylpentyl)-cyclohex-3-ene-1-carbaldehyde.

16. A method according to claim 13, wherein said detergent or said fabric softener contains a compound of formula (I) in which R stands for a group of formula

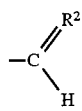

$R^2$ representing a radical derived from a fragrant aldehyde selected from the group consisting of the $C_6$ to $C_{12}$ aldehydes, hydrotropic aldehyde, methyl nonyl acetaldehyde, phenylpropanoic aldehyde, 3- or 4-(4-methyl-3-pentenyl)-3-cyclohexene-1-carbaldehyde, 2-methyldecanal, 4-isopropyl-1-benzeneacetaldehyde, (4-methyl-1-phenyl)acetaldehyde, 6-nonenal, citral, citronellal, 9-decenal, 3-(4-isopropyl-1-phenyl)-2-methylpropanal, 2,4-heptadienal, 2,4-nonadienal, 2,4-decadienal, 5,9-dimethyl-4,9-decadienal, 6-octenal, 2,6,10-trimethyl-9-undecenal, 3-(4-methoxy-1-phenyl)-2-methylpropanal, 3-(1,3-benzodioxol-5-yl)-2-methylpropanal, 4-heptenal, 3, 5,5-trimethylhexanal, (4-methyl-1-phenoxy)-acetaldehyde, hydroxycitronellal, isocyclocitral, 3-(4-tert-butyl-1-phenyl)-2-methylpropanal, 1-p-menthene-9-carbaldehyde, 3- or 4-(4-hydroxy-4-methylpentyl)-3-cyclohexene-1-carbaldehyde, 2,6-dimethyl-5-heptenal, 1-p-menthen-9-al, 2-octenal, 2,6-nonadienal, 3-methyl-5-phenylpentanal, 4-decenal, 2-undecenal, 3,7-dimethyloctanal, 2,4-dimethyl-3-cyclohexene-1-carbaldehyde, 3-phenylbutanal, octahydro-5-methoxy-4,7-methano-1H-indene-2-carboxaldehyde, 2,5, 9-trimethyl-4,9-decadienal, undecenal, 4-methyl-phenyl-propanoic aldehyde and 3-(4-tertbutyl-1-phenyl) propanal.

17. A method according to claim 13, wherein said detergent or said fabric softener contains a compound of formula (I) in which R stands for a group of formula

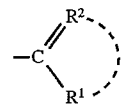

$R^1$ and $R^2$ representing radicals derived from a fragrant ketone selected from the group consisting of 4-(4-hydroxy-1-phenyl)-2-butanone, benzylacetone, an ionone, carvone, 3,7-dimethyl-1,1-bis(11-methyldodecyloxy)-2,6-octadiene, muscone, 2-pentyl-1-cyclopentanone, ethyl amyl ketone, ethyl pentyl ketone, 2-heptyl-1-cyclopentanone, genarylketone, methylionone, 1-(octahydro-2,3,8,8-tetramethyl-2-naphtalenyl)-1-ethanone, 6-methyl-5-hepten-2-one, methyl jasmonate, methyl hexyl ketone, methyl pentyl ketone, methyl nonyl ketone, cis-jasmone, methyl dihydrojasmonate, civettone, 4-(1,1-dimethylpropyl)-1-cyclohexanone, cyclopenta-decanone, 2,6,6-trimethyl-2-cyclohexene-1,4-dione, p-tert-butylcyclohexanone, tricyclo [6.2.1.0$^{2,7}$]undec-9-en-3-one, 10,10-dimethyl-tricyclo [7.1.1.0$^{2,7}$]undec-2-en-4-one, perhydro-5,5,8a-trimethyl-2-naphtalenone and 5-methyl-exo-tricyclo[6.2.1.0$^{2,7}$]undecan-4-one.

18. A method according to claim 13, wherein said detergent or said fabric softener contains a compound of formula (I) selected from the group consisting of 2-phenylethyl octanoate, 2-phenylethyl hexadecanoate, 3,7-dimethyl-6-octenyl octanoate, 3,7-dimethyl-6-octenyl hexadecanoate, 3-methyl-5-phenyl-1-pentyl octanoate, 3-methyl-5-phenyl-1-pentyl hexadecanoate, 7-p-menthanyl octanoate, 9-decenyl octanoate, 9-decenyl-nonanoate, 9-decenyl decanoate, 9-decenyl undecanoate, 9-decenyl dodecanoate, 9-decenyl tridecanoate, 9-decenyl tetradecanoate, 9-decenyl pentadecanoate, 9-decenyl hexadecanoate, 1-methylpentyl hexadecanoate, 7-p-menthanyl hexadecanoate, hexyl hexadecanoate, (Z)-3-hexenyl hexadecanoate, (E)-3,7-dimethyl-2,6-octadienyl hexadecanoate, bis(9-decenyl) oxalate, bis(9-decenyl) malonate, bis(9-decenyl) butanedioate, bis(9-decenyl) pentanedioate, bis(9-decenyl) hexanedioate, (E,E)-bis(3,7-dimethyl-2,6-octadienyl) oxalate, (E,E)-bis(3,7-dimethyl-2,6-octadienyl) malonate, (E,E)-bis(3,7-dimethyl-2,6-octadienyl) butanedioate, (E,E)-bis(3,7-dimethyl-2,6-octadienyl) pentanedioate, (E,E)-bis(3, 7-dimethyl-2,6-octadienyl)hexanedioate, 2-(4-tert-butylbenzyl)-1-propenyl acetate, 3,7-dimethyl-1,6-octadienyl acetate, 3,7-dimethyl-1,6-octadienyl octanoate, 2-methyl-1-undecenyl acetate, 2-methyl-1-undecenyl octanoate, 1-undecenyl acetate, 3-methyl-5-phenyl-1-pentenyl acetate, 3-methyl-5-phenyl-1-pentenyloctanoate, methyl-3-acetoxy-2-pentyl-2-cyclopentene-1-acetate and methyl-3-octanoyloxy-2-pentyl-1-cyclopentene-1-acetate.

* * * * *